US007095676B2

(12) United States Patent
D'Angelo et al.

(10) Patent No.: US 7,095,676 B2
(45) Date of Patent: Aug. 22, 2006

(54) ASSESSING A SOLIDS DEPOSIT IN AN OILFIELD PIPE

(75) Inventors: Ralph M. D'Angelo, New Fairfield, CT (US); Kenneth W. Winkler, Ridgefield, CT (US); David L. Johnson, Bethel, CT (US); Gale Gustavson, Brookfield, CT (US); Oliver C. Mullins, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 488 days.

(21) Appl. No.: 10/112,008

(22) Filed: Mar. 29, 2002

(65) Prior Publication Data

US 2003/0185100 A1 Oct. 2, 2003

(51) Int. Cl.
*G01V 1/40* (2006.01)
(52) U.S. Cl. ............................. 367/31; 367/32; 367/35
(58) Field of Classification Search .................. 367/25, 367/32, 28, 30, 31, 35; 181/105; 73/152.57, 73/599, 609
See application file for complete search history.

(56) References Cited

U.S. PATENT DOCUMENTS

| | | | | |
|---|---|---|---|---|
| 4,742,495 A * | 5/1988 | Medlin et al. | ................ | 367/31 |
| 4,791,619 A | 12/1988 | Liu | .............. | 367/35 |
| 4,813,028 A | 3/1989 | Liu | .............. | 367/31 |
| 4,907,204 A * | 3/1990 | Medlin | ......................... | 367/35 |
| 4,953,137 A * | 8/1990 | Medlin | ......................... | 367/31 |
| 5,357,482 A * | 10/1994 | O'Sullivan et al. | ........... | 367/35 |
| 5,687,138 A | 11/1997 | Kimball et al. | ............... | 367/31 |
| 5,734,588 A * | 3/1998 | Rose et al. | .................... | 73/644 |
| 5,784,333 A | 7/1998 | Tang et al. | .................... | 367/30 |
| 5,999,484 A | 12/1999 | Kimball et al. | ............... | 367/31 |
| 6,192,316 B1 | 2/2001 | Hornby | ......................... | 702/6 |
| 6,470,749 B1 * | 10/2002 | Han et al. | ..................... | 73/622 |
| 6,568,271 B1 * | 5/2003 | Shah et al. | ................... | 73/599 |

FOREIGN PATENT DOCUMENTS

| | | |
|---|---|---|
| FR | 2 754 898 | 4/1998 |
| WO | WO 91/16642 | 10/1991 |

(Continued)

OTHER PUBLICATIONS

Lang, S. W. et al. "Estimating Slowness Dispersion from Arrays of Sonic Logging Waveforms". *Geophysics*, vol. 52, pp. 530-544, (1987).

(Continued)

*Primary Examiner*—Ian J. Lobo
(74) *Attorney, Agent, or Firm*—John L. Lee; Vincent Loccisano; Jody Lynn DeStefanis

(57) ABSTRACT

Tube waves are used to locate and characterize a solids deposit inside a fluid-filled pipe. An acoustic tube wave pulse is transmitted along the pipe. On encountering a solids deposit, the tube wave pulse is perturbed and partially reflected by changes in the boundary conditions between the fluid and the pipe to produce two deposit-modified acoustic waves. One is a perturbed wave travelling in the same direction as the tube wave pulse. The other is a reflected wave travelling in the opposite direction. One of these deposit-modified acoustic waves is received to produce an acoustic signal. Accumulated acoustic signals are processed by Fast-Fourier Transform to produce frequency-based digital data. Phase data from the frequency-based digital data is inverted to produce slowness spectrum data. Power data from the frequency-based digital data is inverted to produce attenuation spectrum data. Spectrum data is used to locate a solids deposit in the pipe. Inversion model processing of the spectrum data is used to estimate solids deposit thickness and type.

22 Claims, 19 Drawing Sheets

FOREIGN PATENT DOCUMENTS

WO    WO 02/08791 A1    1/2002

OTHER PUBLICATIONS

Winkler, K. W. et al. "Technique for Measuring Ultrasonic Velocity and Attenuation Spectra in Rocks Under Pressure". *Journal of Geophysical Research*, vol. 87, No. B12, pp. 10,776-10,780, (Dec. 1982).

Biot, M. A. "Propagation of Elastic Waves in a Cylindrical Bore Containing a Fluid". *J. Appl. Phys.*, vol. 23, pp. 997-1005, (Sep. 1952).

* cited by examiner

ASSESSING A SOLIDS DEPOSIT IN AN OILFIELD PIPE

The present invention is related to U.S. Pat. No. 4,813,028, issued Mar. 14, 1989, U.S. Pat. No. 5,687,138, issued Nov. 11, 1997, and U.S. Pat. No. 5,999,484, issued Dec. 7, 1999, all assigned to Schlumberger Technology Corporation, Houston, Tex., the assignee of the present invention.

FIELD OF THE INVENTION

The present invention relates to methods and apparatus for detecting and characterizing a solids deposit on the inside of an oilfield production pipeline.

BACKGROUND OF THE INVENTION

Deepwater oil production is a rapidly growing segment of the oil industry. As the number of deepwater installations increase, so do the problems with maintaining sub-sea fluid transport systems. Sub-sea equipment, including pipelines, are becoming clogged with precipitates of the production fluids, including waxes, asphaltenes, hydrates (gas/water ices) and scale (e.g. calcium carbonate). Similarly, production tubing in producing wells can develop flow-restricting deposits, usually of the asphaltene type. There are significant problems because of the enormous cost of lost production, and because of the very large expenses involved in identifying and replacing, or bypassing, the constricted or blocked sections of pipe. The industry refers to these and related issues as "Flow Assurance". In 1999 Welling and Associates, having conducted a world-wide study of 110 oil and gas companies, found that flow assurance was the most important technical challenge facing the oil and gas industry. Connective pipelines, manifolds and risers can total hundreds of kilometers (i.e. hundreds of miles) in length, and operate at water depths of up to approximately 3,000 m (approximately 10,000 ft). Maintenance over these distances and at these depths is very costly. Deposits often occur in one region of a pipe, spanning many meters (many feet), but not extending over the entire pipe length. The chemistry of formation of the different types of deposit is at least partially understood. Gas cut, flow rate, and temperature at depth are all relevant factors. This knowledge facilitates identification of locations where deposits can be expected to occur. However, the first indication that deposition is occurring is usually a reduction in flow rate, which is too late.

Thus, the industry needs a cost-effective method for detecting and characterizing solids deposits inside oilfield production pipelines to improve flow assurance. Currently, no cost-effective methods are available.

SUMMARY OF THE INVENTION

Tube waves are used to locate and characterize a solids deposit inside a fluid-filled pipe. An acoustic tube wave pulse is transmitted along the pipe. On encountering a solids deposit, the tube wave pulse is perturbed and partially reflected by changes in the boundary conditions between the fluid and the pipe to produce two deposit-modified acoustic waves. One is a perturbed wave travelling in the same direction as the tube wave pulse. The other is a reflected wave travelling in the opposite direction. One of these deposit-modified acoustic waves is received to produce an acoustic signal. Accumulated acoustic signals are processed by Fast-Fourier Transform to produce frequency-based digital data. Phase data from the frequency-based digital data is inverted to produce slowness spectrum data. Power data from the frequency-based digital data is inverted to produce attenuation spectrum data. Spectrum data is used to locate a solids deposit in the pipe. Inversion model processing of the spectrum data is used to estimate solids deposit thickness and type.

One embodiment of the apparatus of the invention uses a permanent-sensor instrumented pipe having an acoustic transmitter and an array of receivers. Another embodiment uses a permanent-sensor instrumented pipe having an array of transmitter/receivers. Another embodiment uses a logging tool having an acoustic transmitter and an array of receivers. Another embodiment uses a logging tool having an array of transmitter/receivers.

BRIEF DESCRIPTION OF THE DRAWINGS

FIG. 16 also shows a representative waveform from the scan used to produce the variable-density plot.

DETAILED DESCRIPTION OF THE INVENTION

Figure 1:
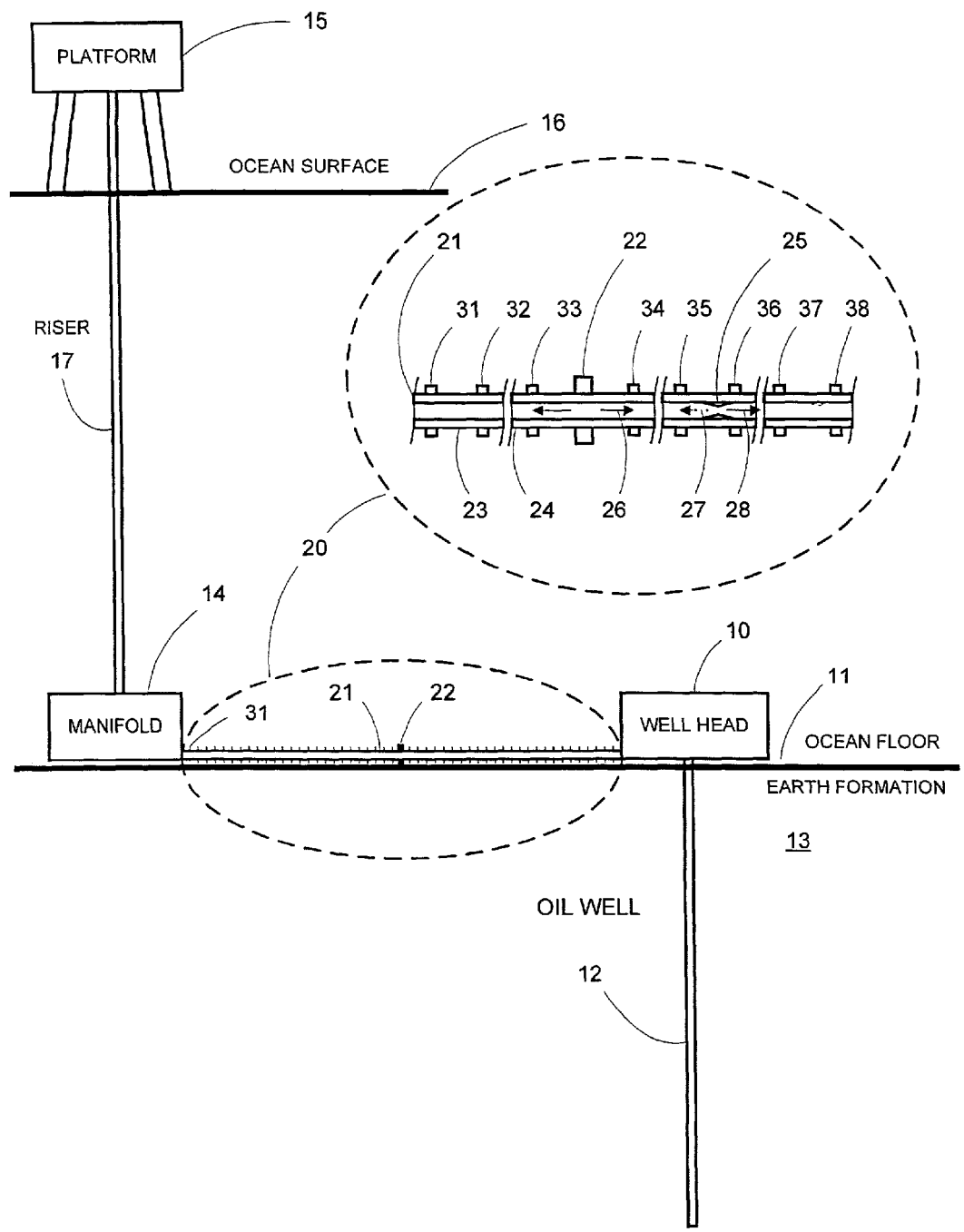
FIG. 1 illustrates a first preferred embodiment of an instrumented transport pipe having pipe-mounted receivers positioned to detect perturbed tube waves for detecting and characterizing a solids deposit in a sub-sea pipeline.

The applicants recognized that to solve the problems of flow assurance as discussed above under Background of the Invention, a measurement system is needed capable of early detection of solids deposits on the inside of sub-sea pipes and risers used in oil and gas production, and on the inside of production tubing used in standard production wells. The applicants further recognized that such a measurement system must be capable of determining the location of any solids deposit detected, and preferably should also be capable of determining the thickness, length, and type of material of the solids deposit.

The applicants propose a method and apparatus for assessing a solids deposit inside a fluid-filled pipe using a tube wave. A tube wave, or a "hammer mode" wave, travels predominantly in the fluid of a fluid-filled pipe. Its energy is trapped in the fluid, confined by the walls of the relatively rigid containing pipe. A tube wave is known to be capable of carrying energy very efficiently over great distance in a fluid-filled pipe. Energy propagates in a tube wave pulse along the pipe, and is perturbed and partially reflected by changes in the boundary conditions between the fluid and the pipe.

The applicants further propose inverting a perturbed tube wave to take advantage of the rigorous mathematical theory available for inversion of tube waves. Inverting the perturbed tube wave allows the measurement system to determine, for example, the average thickness of a solids deposit. Under some circumstances, the use of inversion facilitates identification of the type of deposit, e.g. whether the solids deposit is predominately wax, asphaltene, hydrate or scale.

The applicants further propose receiving a deposit-modified tube wave, i.e., either a "perturbed" tube wave, or a "reflected" tube wave. In either case, the technique would provide early detection of a solids deposit, determination of the location of the solids deposit, and determination of the characteristics of the solids deposit.

The applicants propose that preferably a tube wave be used because the propagation characteristics of a tube wave match the very long lengths of sub-sea pipelines. So the measurement system lends itself to economical implementation.

The present invention provides a monitoring system for early detection of a solids deposit on the inside of a pipe by transmitting an acoustic tube wave along the pipe and detecting a received acoustic wave perturbed by any solids deposit existing in the pipe. In the preferred embodiment, the monitoring system further includes means for generating position data for determining the location of the solids deposit. The position data includes location of the solids deposit as being between two specific receivers, or alternatively distance data calculated from time of flight. The preferred embodiment further includes means for characterizing the solids deposit by inverting a received tube wave perturbed by the solids deposit. Characterizing the solids deposit includes determining the average thickness of the solids deposit.

The applicants further recognized that such a measurement system would be capable of detecting and determining the location of a solids deposit in a sub-sea pipeline, in a sub-sea riser, in a surface pipeline, or in the production tubing of an oil well.

The applicants further recognized that it is easy to excite and receive a tube wave from outside the pipe because tube waves that propagate in typical oilfield pipes have wavelengths that are many times longer than the pipe's wall-thickness, and that this approach offers advantages under some circumstances.

The applicants further recognized that tube waves could be utilized over long spans of pipe because tube waves are very energetic and subject to small losses under typical oilfield pipeline conditions.

The applicants recognized that ultrasonic techniques used in evaluating cement-formation interface could be used to detect solids deposits on the inside of sub-sea pipes and risers. However, applicants note that the ultrasonic approach has two major disadvantages for oilfield pipe application. First, the reflection coefficient of the solids-deposit\fluid interface is very small, so sensitivity is low. Second, ultrasonic techniques can be used effectively only for localized measurements. So hundreds of ultrasonic devices would be needed at intervals along the several miles of pipeline. Even then, a local measurement showing good, clean pipe may be just a few meters (a few feet) away from the beginning of a hydrate formation or a wax build-up.

The Apparatus of the First Embodiment

FIG. 1 shows a sub-sea oil production system including a first preferred embodiment of a permanent-sensor flow assurance measurement system for detecting and characterizing (i.e., assessing) a solids deposit in a fluid-filled sub-sea transport pipe. This embodiment includes a first preferred embodiment of an instrumented pipe, instrumented transport pipe 20. The instrumented pipe includes a pipe 21, and a transmitter 22 attached to the pipe. The transmitter is adapted to transmit a first acoustic tube wave pulse along the pipe. The instrumented pipe further includes pipe-mounted receivers 31, 32, etc., positioned to detect a perturbed tube wave and to produce an acoustic signal.

The system further includes a processor (not shown) for processing acoustic signals to determine the value of a selected characteristic of an acoustic wave indicative of a solids deposit in a fluid-filled pipe.

FIG. 1 shows instrumented pipe 20 as a sub-sea transport pipe in context of the sub-sea oil production system. The sub-sea oil production system includes well head 10 located at ocean floor 11, and oil well 12 extending downward into earth formation 13. In production, oil from the well is pumped through transport pipe 21 to manifold 14. Typically, multiple transport pipes are connected in like manner to manifold 14. Oil from the several transport pipes is pumped to platform 15 at ocean surface 16 via riser 17. Instrumented transport pipe 20 includes transport pipe 21, a single centrally located transmitter 22, and first and second periodic arrays of twenty two receivers mounted along transport pipe 21, one array on each side of the transmitter as represented by a receivers 31–33 and 34–38, respectively.

In the embodiment of FIG. 1, transport pipe 21 is approximately one third of a mile (500 meters) long, and the receivers are spaced at approximately 30 foot (10 meter) intervals. Because transport pipe 21 is short, only a single flow assurance measurement system is used. A single flow assurance measurement system consists of a single transmitter and multiple receivers, located on both sides of the transmitter. An installation having a very long transport pipe, e.g. 1 mile (1600 meters) or more, would preferably include multiple flow assurance measurement systems. To accommodate the long pipes involved, each transport pipe 21 is made of a plurality of pipe joints connected in series. Thus, the permanent transmitter(s) and the receivers are distributed over a plurality of pipe joints.

The inset in FIG. 1 is a schematic illustration of instrumented transport pipe 20. The inset shows transport pipe 21, transmitter 22, and receivers 31–38 representing the forty-four receivers. The inset also shows instrumented pipe joint 23 having two receivers 31 and 32, and instrumented pipe joint 24 having one transmitter 22 and two receivers 33 and 34.

Transmitter 22 is adapted to transmit a first acoustic tube wave along the pipe. Tube waves propagating in both directions from transmitter 22 are utilized. The transmitter energy couples easily into transport pipe 21 to produce a first acoustic tube wave 26. First acoustic tube wave 26 propagates in the fluid in the pipe, along the axis of the pipe. When first acoustic tube wave 26 encounters solids deposit 25, it produces reflected tube wave 27 and perturbed tube wave 28. Perturbed tube wave 28 is detected by receivers 37 and 38. The receivers also couple easily into transport pipe 21. Each receiver receives perturbed tube wave 28 and produces an acoustic signal therefrom.

Receiver to receiver spacing used in a flow assurance measurement system is selected to provide the spatial resolution needed to define the location of a solids deposit (location can only be determined as being between two specific receivers), and by the degree of sensitivity needed to detect small, localized deposits. For typical applications, receiver to receiver spacing of about 100 ft (about 30 meters) is recommended.

The span of the flow assurance measurement system may be on the order of several hundred feet to several miles (several hundred meters to a several kilometers), from the left-most receiver, 31, to the right most receiver 38. The maximum span of a single flow assurance measurement system is limited by the loss suffered as the acoustic wave traveling along the pipe is attenuated. If attenuation is high, span must be limited to achieve sufficient wave energy at the receivers furthest from the transmitter. If the wave attenuation is very low, spans of multiple miles may be possible. It is also recognized that span lengths are determined by locality requirements. That is, a region along the pipe layout having high probability of solids deposits may be very short, and may require only a few hundred feet of measurement system span.

Multiple flow assurance measurement systems may be deployed along the same pipe or pipe system, allowing for complete coverage in pipes of great lengths (many miles), where the attenuation of the acoustic wave does not allow transmission along the entire pipe length.

Multiple systems may also be used in applications where the pipe-layout design suggests several specific regions that are likely for solids deposits, but where coverage is generally not needed along the entire length. In these situations, several shorter inspection systems may be used.

The transmitters of the multiple systems deployed on a pipe may be fired simultaneously, or independently. The systems can be viewed as acoustically independent, because a signal received at a specific receiver is referenced in time to its associated transmitter.

Transmitters and receivers for this embodiment preferably have transducer elements made from suitable ceramics such as circular piezoelectric ceramics type K350, having a center-frequency of 200 KHz (thickness-poled). These ceramics are available from Keramos, Inc., Indianapolis, Ind. They are installed permanently around the inside of the pipe or the outside of the pipe, preferably completely around the outside of the pipe. However, partial coverage is acceptable. Other suitable device-types are circular electromagnetic acoustic transducers ("emats"), and electro-mechanical devices including hammer/solenoids, and fluid pumps or fluid-sirens as used in LWD mud-pulse telemetry. Most of these device-types can be used either as a transmitter or as a receiver.

Method of the First Embodiment

Figure 10:
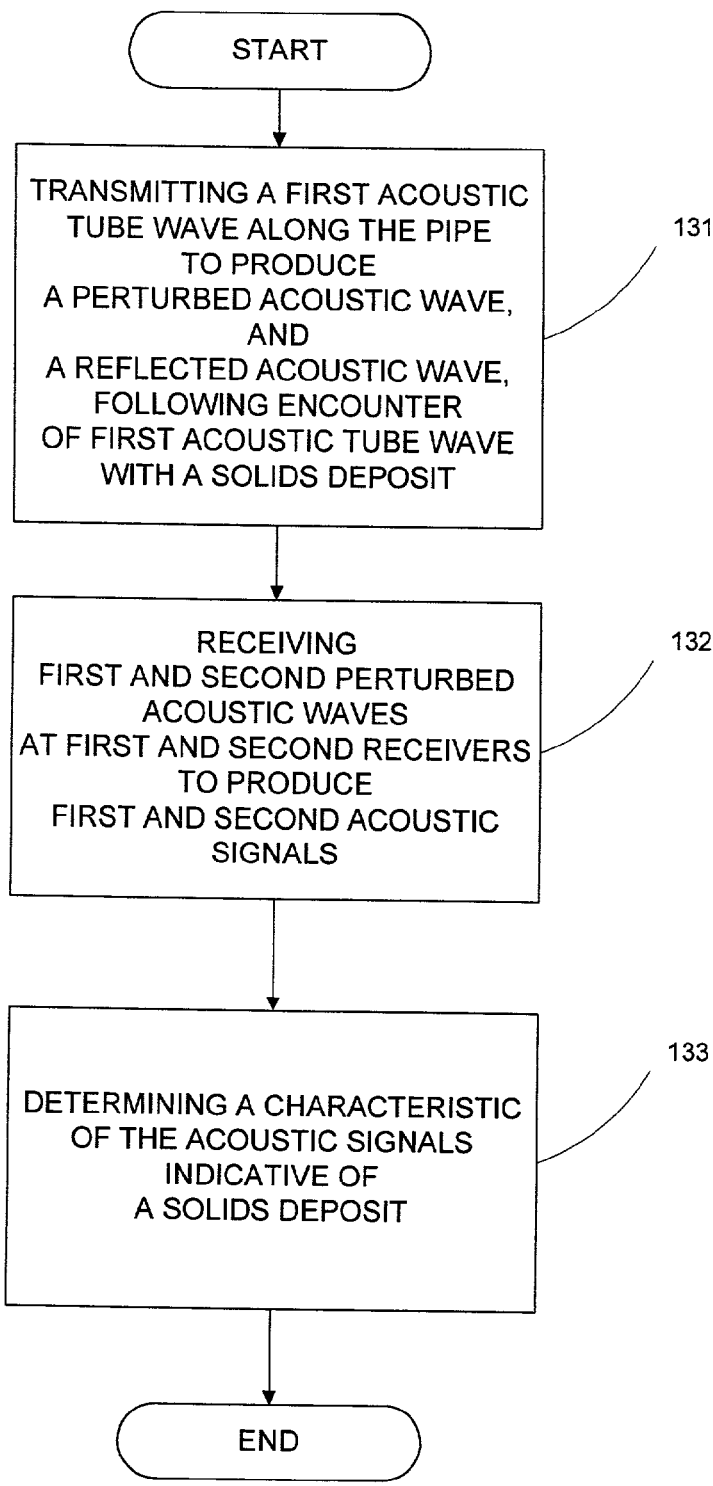
FIG. 10 illustrates the preferred embodiment of the method illustrated in FIG. 9.
Figure 11:
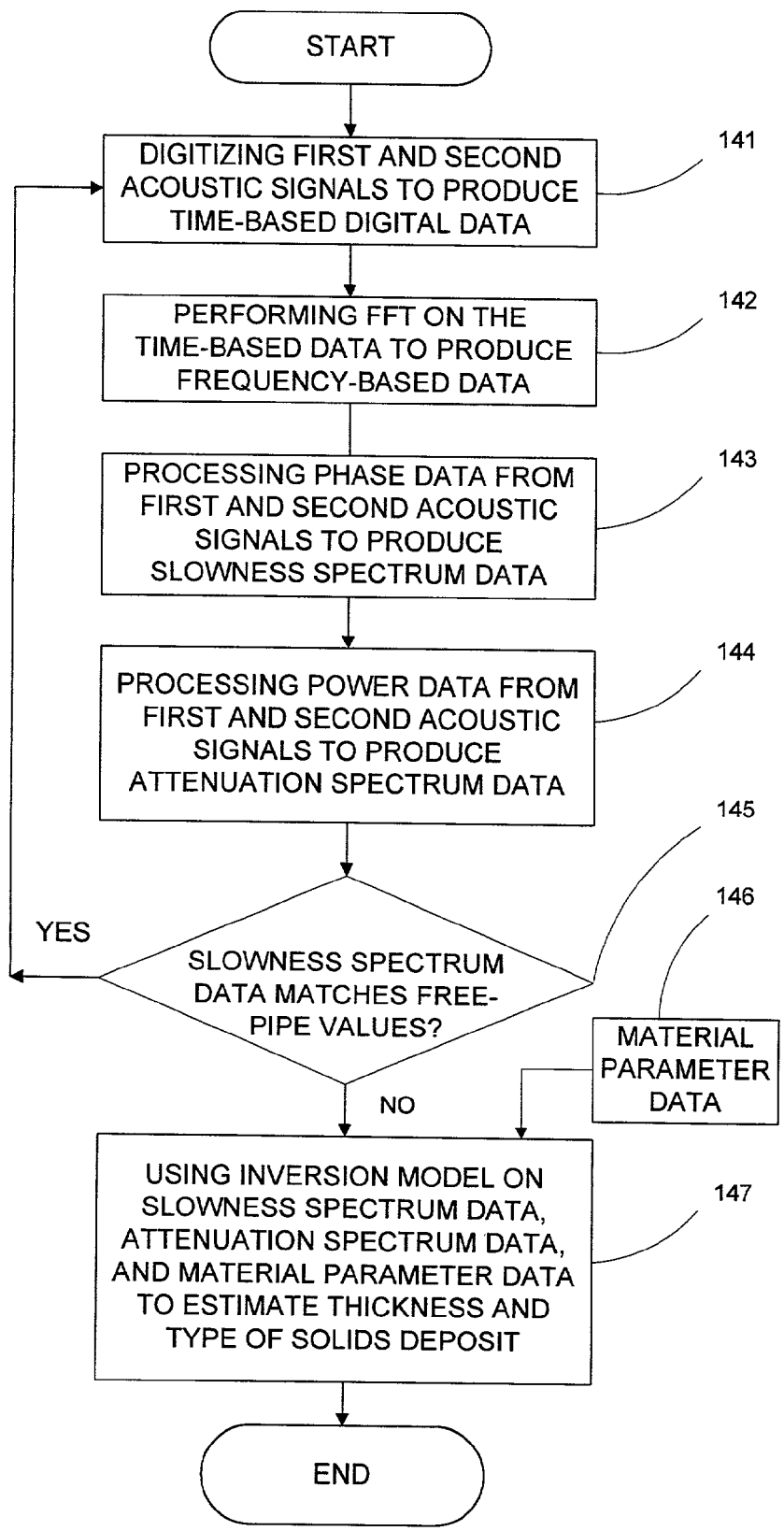
FIG. 11 gives further detail of the preferred embodiment.

The first preferred embodiment of the method of the present invention, illustrated in FIGS. 10 and 11, is based on measuring time of travel of a tube wave to determine slowness inverse velocity, and measuring power in the tube wave to determine attenuation. Time of travel is determined by counting time from the firing of a transmitter to produce a tube wave pulse to receipt of a signal from an associated receiver.

The first preferred embodiment uses inversion to determine slowness spectrum data and attenuation spectrum data. Determining slowness spectrum data involves subtracting phase at a second receiver from phase at a first receiver to produce a phase difference, multiplying the phase difference by frequency, and dividing the result by the distance between the first and second receivers. Determining attenuation spectrum data involves subtracting power at a second receiver from power at a first receiver to produce a power difference, and dividing the result by the distance between the first and second receivers. Any difference between the newly determined slowness spectrum data and the original free-pipe slowness spectrum data is indicative of a deposit between the receivers. Step 145 in FIG. 11 tests for match. If the data match, there is no deposit between the receivers. If the data do not match, a solids deposit has been detected. Thickness and the type of the deposit is determined using the inversion model on slowness and attenuation spectrum data.

As a first acoustic tube wave travels along a fluid-filled pipe, predominantly travelling in a direction aligned with the pipe, it will be acted upon by any solids deposits encountered, in a manner consistent with known acoustic scattering theory. Upon encountering a solids deposit, the first acoustic wave will produce two deposit-modified acoustic waves, a perturbed wave and a reflected wave. FIG. 1 shows perturbed wave 28 leaving the area of solids deposit 25 and travelling in the same direction as first acoustic wave 27, and reflected wave 27 leaving the area of solids-deposit 25 and travelling in the opposite direction of first acoustic wave 27.

As illustrated in FIGS. 1 and 9–11, the first preferred embodiment of the method for assessing a solids deposit inside a fluid-filled pipe includes transmitting a first acoustic tube wave (26 in FIG. 1) along the pipe. Two deposit-modified acoustic tube waves in the form of a perturbed wave and a reflected wave are produced when the first acoustic tube wave encounters a solids deposit in the pipe.

The method further includes receiving a deposit-modified acoustic wave to produce an acoustic signal, and determining the value of a selected characteristic of the acoustic signal indicative of a solids deposit in the pipe.

Each transmitter transmits a tube wave as a pulse. The signal from a given receiver is accepted within a time window corresponding to the firing time of its associated transmitter. This filters out unwanted signals from the given receiver that are produced by tube waves from other transmitters.

In the first preferred embodiment, receiving a deposit-modified acoustic wave is receiving a perturbed tube wave at spaced-apart first and second receivers (receivers 34 and 35 in FIG. 1). The receivers produce first and second acoustic signals. Determining the value of a selected characteristic includes the acts of:

(a) digitizing said first and second acoustic signal to produce time-based digital data;
(b) performing a Fast-Fourier Transform (FFT) on said time-based digital data to produce frequency-based digital data;
(c) processing phase data at first and second receivers to produce slowness spectrum data;
(d) processing power data at first and second receivers to produce attenuation spectrum data;
(e) determining slowness of the acoustic signal indicative of a solids deposit;
(f) using inversion model on slowness and attenuation spectrum data to estimate thickness and type of solids deposit;

Step (c) includes the acts of:

(g) subtracting phase at a first receiver from phase at a second receiver to produce, for each of a plurality of frequencies, a phase difference; and
(h) multiplying each phase difference by its associated frequency; and dividing the result by the distance between said first and second receivers to produce slowness spectrum data.

In the first preferred embodiment, determining the value of a selected characteristic further includes (1) subtracting power received at the second receiver from power received at the first receiver to produce, for each of a plurality of frequencies, a power difference, and (2) dividing the power difference by the distance between the first and second receivers to produce attenuation spectrum data.

In the first preferred embodiment, determining the value of a selected characteristic further includes determining the thickness of the solids deposit by model-based inversion. Model-based inversion includes processing the slowness spectrum data, the power spectrum data, and using material parameter data derived from an engineering judgement determination of the most likely deposited material.

The location of the solids deposit is determined as being between the first and second receivers.

The direction of an incoming perturbed wave at a given receiver, and therefore the direction of a solids deposit, is determined by comparing the output of the given receiver with the output of a neighboring receiver. The receiver that receives the perturbed wave first from a given transmitter is closer to the solids deposit.

Figure 2:
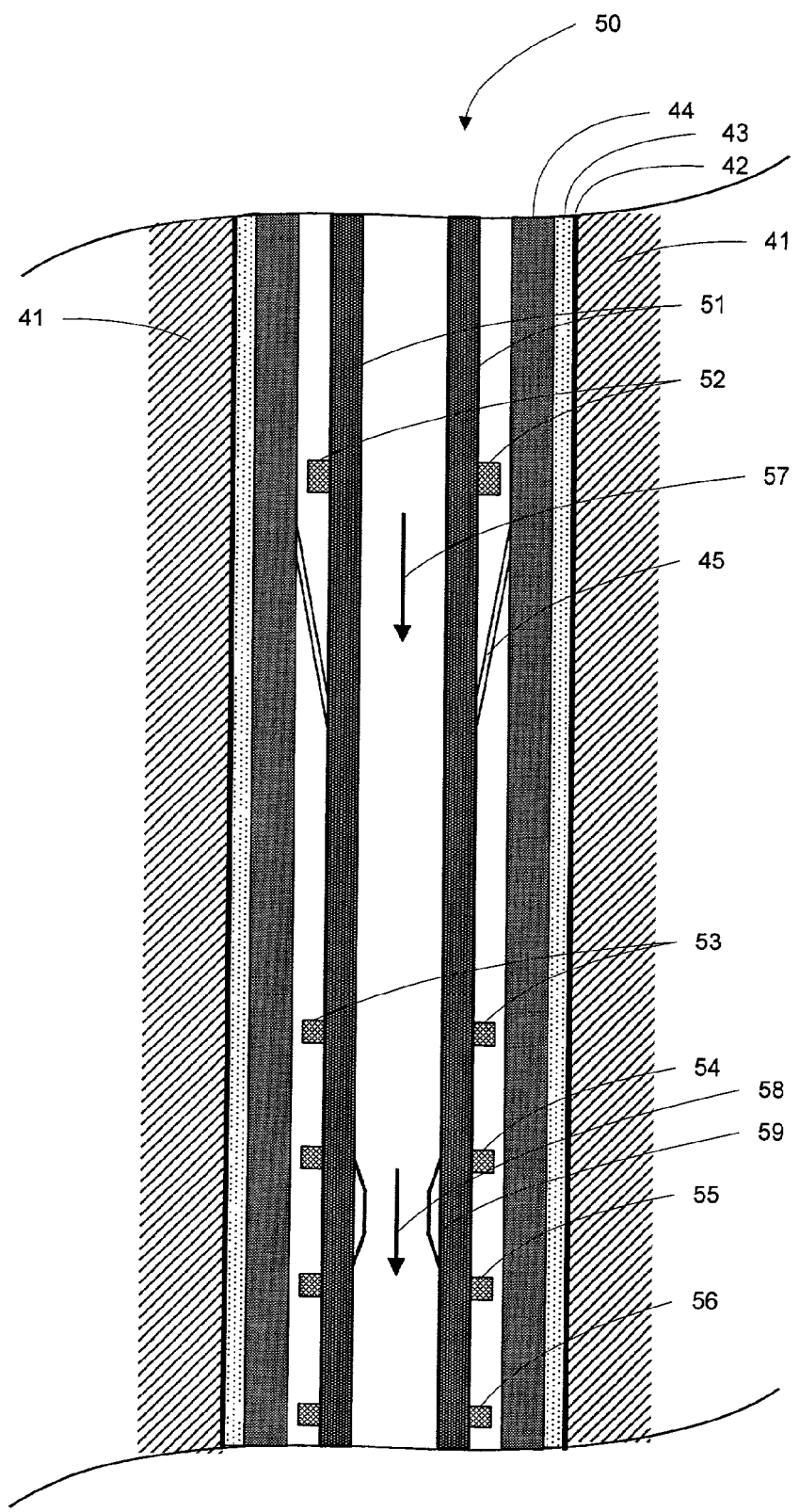
FIG. 2 illustrates a second embodiment of an instrumented oil well production pipe having pipe-mounted receivers positioned to detect perturbed tube waves for detecting and characterizing a solids deposit in an oil well.

Methods for characterizing a solids deposit using the apparatus of FIGS. 1 and 2 are illustrated in FIGS. 9–13 as follows.

Figure 8:
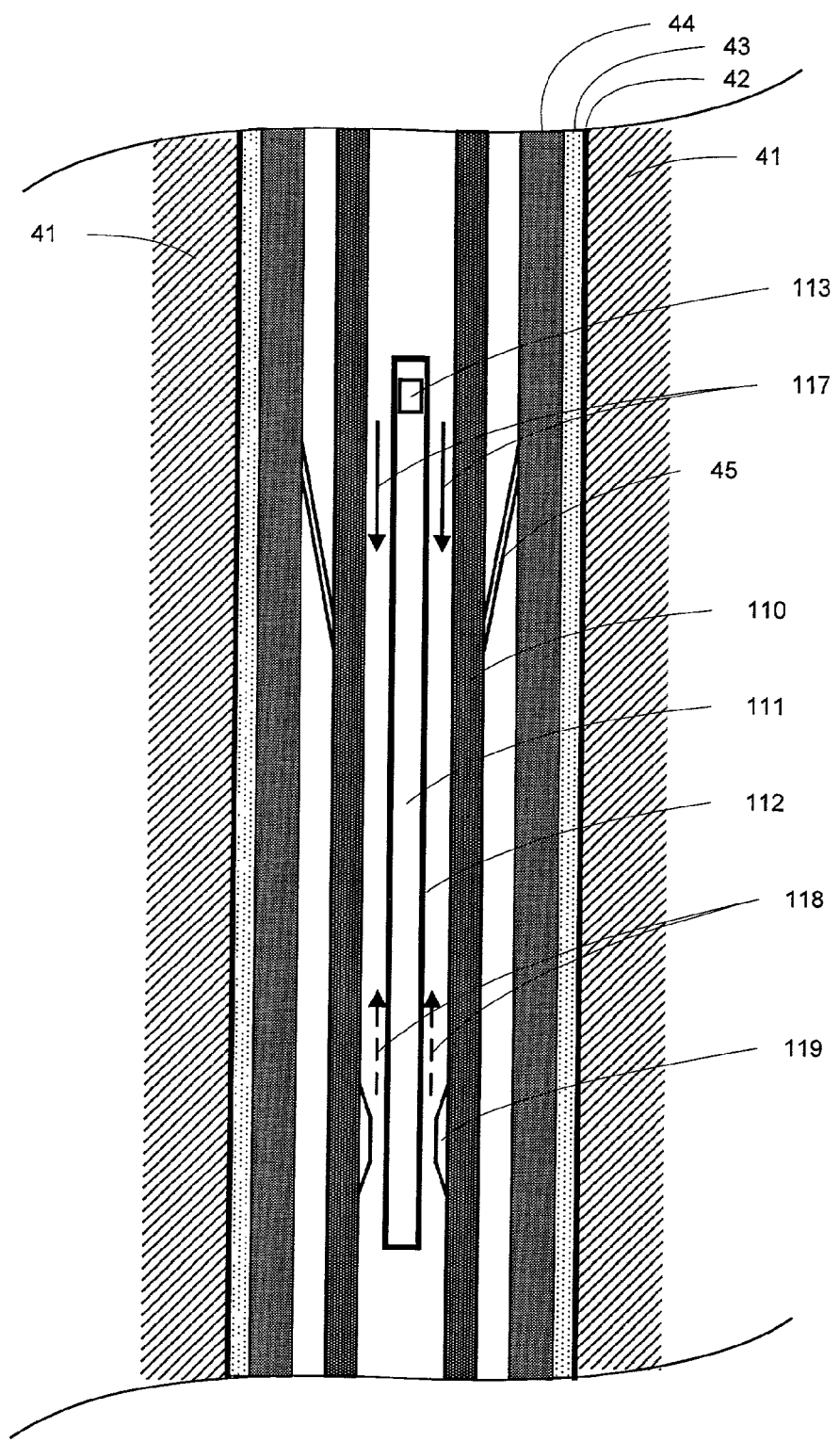
FIG. 8 illustrates a fourth embodiment of a wireline tool for use in an oil well production pipe, the tool having a transmitter/receiver positioned to transmit tube waves along the pipe and to detect reflected tube waves.
Figure 9:
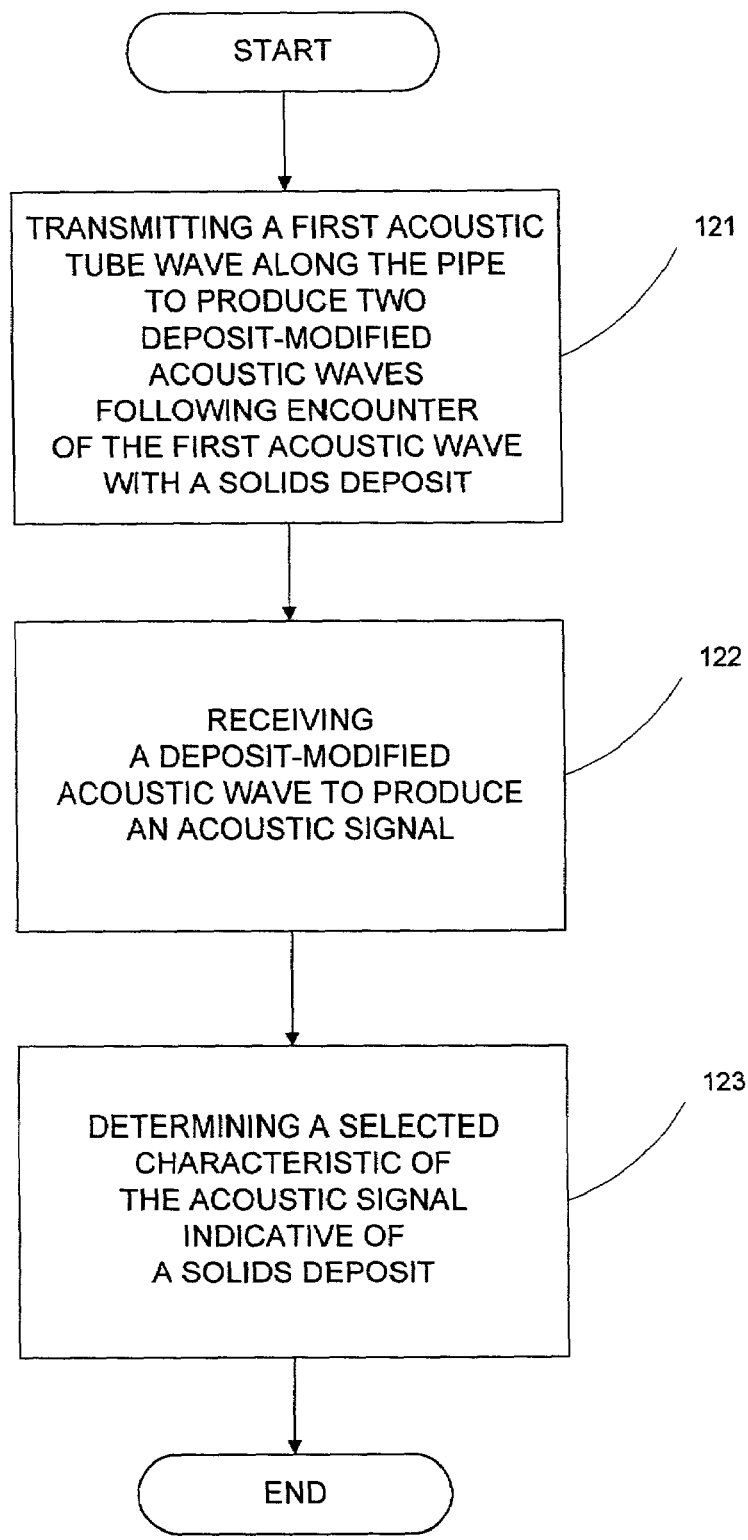
FIG. 9 illustrates the general method of the present invention for assessing a solids deposit inside a pipe.

FIG. 9 illustrates the general method of the present invention for assessing a solids deposit inside a pipe. The method includes receiving a perturbed tube wave and determining a selected characteristic as indicative of a solids deposit inside a pipe. This method may be used with equipment shown in any of FIGS. 1–8

FIG. 10 illustrates the preferred embodiment of the method illustrated in FIG. 9. The preferred embodiment includes receiving a transmitted perturbed tube wave and determining slowness as indicative of a solids deposit inside a pipe. This method may be used with equipment shown in any of FIGS. 1–2 and 5–6.

FIG. 11 gives further detail of the method of FIG. 10. FIGS. 10 and 11 together illustrate the preferred method of the present invention.

Figure 12:
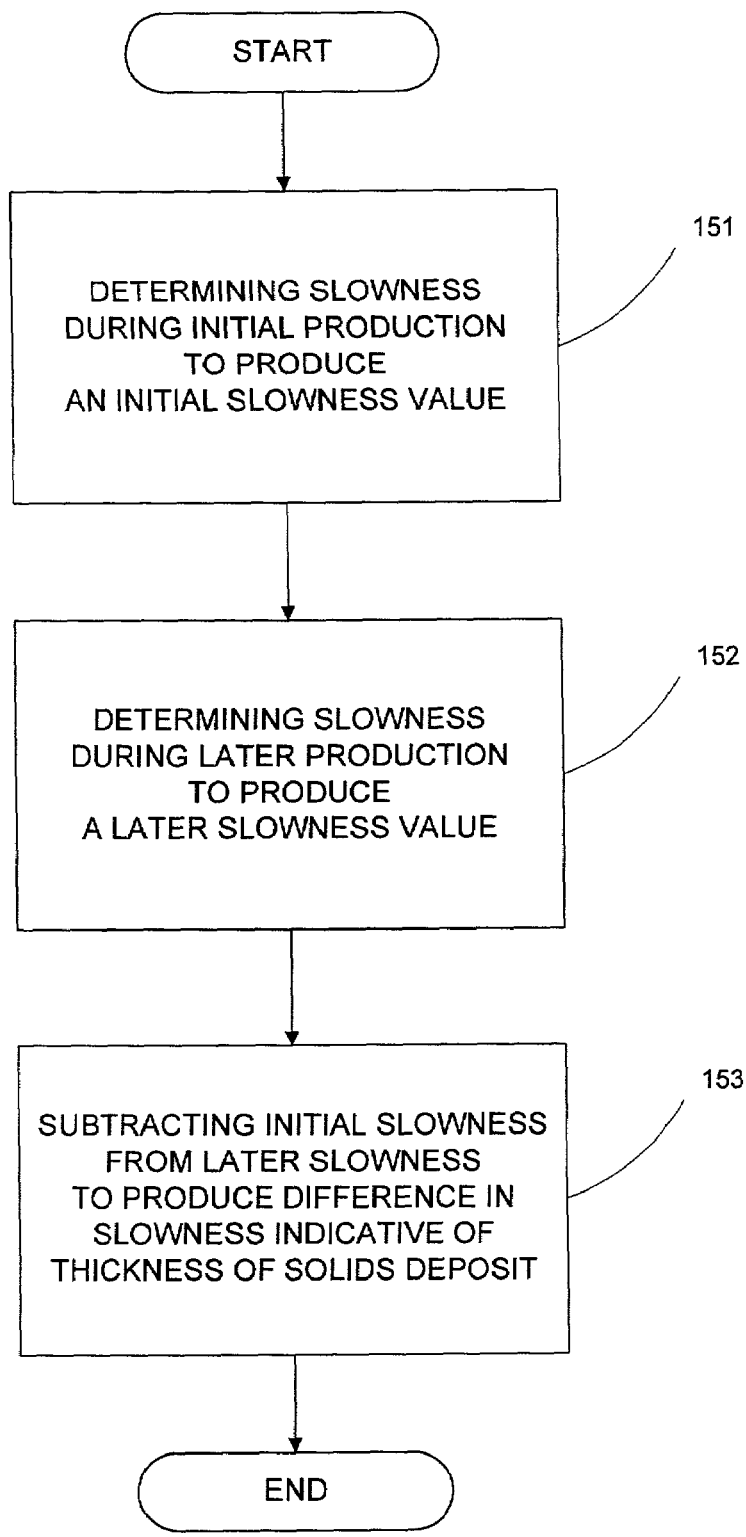
FIG. 12 illustrates a method for comparing current flow capacity of a production pipe with flow capacity of the "clean" production pipe prior to production.

FIG. 12 illustrates a method for comparing current flow capacity of a production pipe with flow capacity of the "clean" production pipe prior to production. This method uses the difference in slowness of transmitted perturbed tube waves (obtained by subtracting slowness prior to production from current slowness) as an indicator of solids deposit and flow capacity. This method may be used with equipment shown in any of FIGS. 1–2 and 5–6. A first alternative method (not shown) uses changes in attenuation of transmitted perturbed tube waves over time as an indicator. A second alternative method (not shown), that may be used with equipment shown in any of FIGS. 3–4 and 7–8, uses changes in attenuation of reflected perturbed tube waves over time as an indicator.

Figure 13:
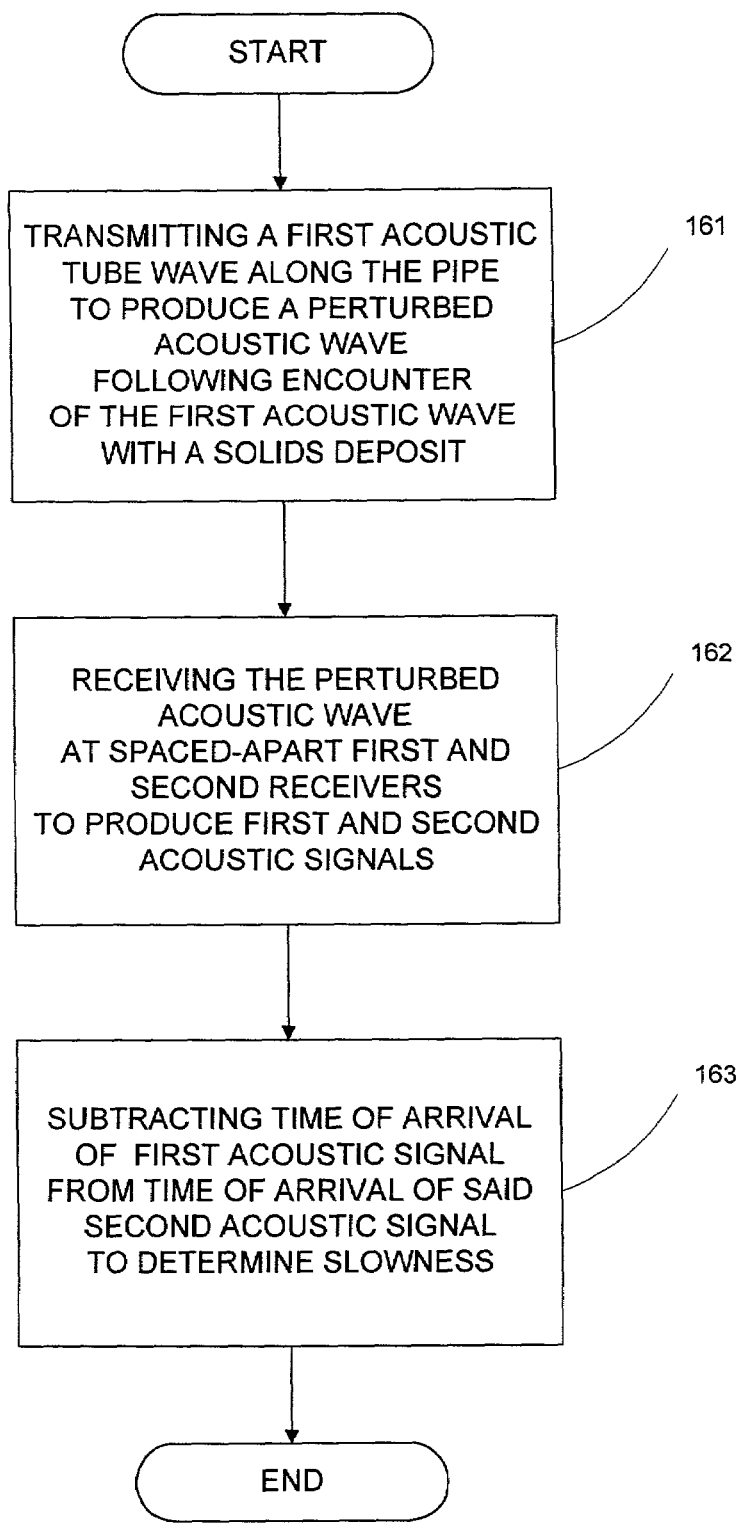
FIG. 13 illustrates a method for assessing a solids deposit inside a pipe using perturbed tube waves, and using slowness as measured by differential time of arrival as an indicator of solids deposit.

FIG. 13 illustrates a method for assessing a solids deposit inside a pipe using transmitted perturbed tube waves, and using slowness as measured by differential time of arrival as an indicator of solids deposit.

In another embodiment, the first acoustic wave is a tube wave, receiving a deposit-modified acoustic wave is receiving a perturbed wave at spaced-apart first and second receivers to produce first and second acoustic signals, and determining the value of a selected characteristic includes subtracting time of arrival of the first acoustic signal from time of arrival of the second acoustic signal to determine slowness.

Another embodiment includes locating one or more transmitters at fixed positions in the pipe and moving a pair of receivers within the interior of the pipe to a succession of positions along the pipe.

Another embodiment includes moving one transmitter and a distant pair of spaced-apart receivers within the interior of the pipe to a succession of positions along the pipe. This is similar to conventional "wireline logging" in a production oil well or "pigging" in a production transport pipe.

In another embodiment, the first acoustic wave is a tube wave, the deposit-modified acoustic wave is a perturbed wave, and the selected characteristic is attenuation.

Another embodiment includes moving one transmitter/receiver within the interior of the pipe to a succession of positions along the length of the pipe.

In another embodiment, the selected characteristic is slowness, and the method further includes determining an initial value of the selected characteristic during initial production; determining a later value of the selected characteristic during production; and subtracting the initial value from the later value to produce a difference value indicative of an increase in thickness of a solids deposit. Preferably this embodiment further includes using the difference value together with material parameter data of a selected deposited material to produce an estimate of thickness of the solids deposit, wherein the elected deposited material is selected based on an engineering determination of most likely deposited material.

In another embodiment, the first acoustic wave is a tube wave, the deposit-modified acoustic wave is a reflected wave, and the selected characteristic is power.

Another embodiment includes determining an average value of slowness over a length of pipe adjacent to a transmitter, and locating the solids deposit using the equation:

distance=(transit time)/(2*average slowness)

Further Description of the Preferred Method

As shown in FIG. 1, when transmitter 22 is fired, a tube wave travels out from it, in both directions along the axis of pipe 21, traveling primarily in the fluid in the pipe. This propagating wave is captured as a voltage signal at all forty-four receivers (represented by receivers 31–38) in the inspection system. The signal passes from the receiver, through standard signal conditioners such as amplifiers and filters, and then to a digitizer where it is captured and stored as a digital signal. The signal from a given receiver is accepted within a time window corresponding to the firing time of its associated transmitter. Since solids deposits accumulate very slowly, on a time-scale of weeks to months, multiple signals may be averaged over periods of minutes or hours without reducing sensitivity to a solids deposit or accuracy of a thickness determination. This technique is used to improve sensitivity of the digitized signal and to reduce short-time variations in the signal that may be caused by a gas bubble or solids traveling in the fluid in the pipe, variations in flow conditions, or other, asynchronous acoustic sources.

The averaged, digital signals obtained at each receiver are then processed in a manner so as to produce a local, inter-receiver dispersion curve of both the slowness and the attenuation found in the tube-wave traveling between the respective receivers. This is accomplished by first, processing each receiver's digital signal into an FFT, providing a phase-spectrum and a power-spectrum over frequency. Then the phase-spectrum data, of two space-separated receivers, is used in calculation with the inter-receiver spacing to compute a slowness-dispersion curve, representative of the tube-wave slowness between the respective receivers. Similarly, the amplitude-spectrum data, of two space-separated receivers, is used in calculation with the inter-receiver spacing to compute an attenuation-dispersion curve, representative of the tube-wave attenuation between the respective receivers. Techniques for processing digital signal from multiple of receivers into an FFT to provide phase-spectrum data as a function of frequency, and power-spectrum data as a function of frequency, are known in the prior art. See "Technique for Measuring Ultrasonic Velocity and Attenuation Spectra in Rocks Under Pressure", K. W. Winkler and T. J. Plona, Journal of Geophysical Research, vol. 87, no. B12, Dec. 10, 1982.

More specifically, the slowness-dispersion data and attenuation-dispersion data is calculated for the tube-wave propagation between receivers 34 and 35 (no intervening deposits). The same dispersion data of the tube-wave is obtained for the receiver-spans between 37 and 38. Each dispersion data set of amplitude and slowness, obtained between each receiver pair, is compared to the expected values for the specific pipe and fluids. A mode-search model is used to calculate the values for attenuation-dispersion and slowness-dispersion that would be obtained for the specific pipe parameters and the specific fluid parameters, under the assumed conditions of a free, or clean, pipe wall (no deposits). A suitable mode search model is described in reference: M. A. Biot, (1952), "Propagation of Elastic Waves in a Cylindrical Bore Containing a Fluid", J. Appl. Phys. v. 23, p. 997–1005). Dispersion data (for amplitude and slowness) at each receiver-pair is then compared to the free-pipe, model data.

The velocity and slowness dispersion data obtained (as between receivers 34 and 35 having no intervening deposits) will match the model's free-pipe data because there is no solids deposit between these receivers. The velocity and slowness dispersion data obtained (as between receivers 35 and 36 with intervening deposits) would not match the model's free-pipe data because there is a solids deposit between these receivers. Thus, a match indicates no solids deposit, and mismatch indicates the presence of solids deposit.

The solids material located between receivers 35 and 36 is analyzed to estimate thickness using a model-based inversion algorithm. This technique assumes a uniform distribution of depositional material across the pipe region between the receivers.

Prior knowledge of the pipe layout and surrounding environmental factors, plus the petrochemical parameters of the specific fluids in the pipe, allows production engineers to estimate the solids material type expected at the specific location indicated as containing a solids deposit, i.e., between receivers 35 and 36. The four most common or likely possibilities are wax, asphaltenes, scale, and hydrates. The parameters of the material selected as the likely candidate are then entered into the model, and the model is run for various thickness of uniform deposition. The slowness and attenuation dispersion curves obtained are compared to the measured (flagged) data for each thickness value run, until a match exists. The thickness producing the best match of slowness and attenuation dispersion curves is pronounced as the average thickness of the solids deposition in this region of the pipe.

In the preferred method described above, the receivers are used to measure slowness. In alternative versions of the method, the receivers are used to measure attenuation.

For situations where multiple receivers are spanned by the solids deposit, an array processing technique, and specifically TKO processing, is preferred. TKO is a frequency-based technique for sonic waveform processing that provides slowness and attenuation data as a function of frequency. TKO processing is described in the reference: Lang, S. W., Kurkjian, A. L., McClellan, J. H., Morris, C. F., and Parks, T. W., 1987, "Estimating slowness dispersions from arrays of sonic logging waveforms": Geophysics, 52, 530–544. TKO processing produces robust, high quality slowness and attenuation data.

Embodiments Grouped by Apparatus

FIGS. 1, 3, 5 and 7 show four embodiments of the apparatus of the present invention applied to oil well transport pipes. FIGS. 2, 4, 6 and 8 show four corresponding embodiments applied to oil well production pipes.

Embodiments Grouped by Method

1) Instrumented Pipe, Perturbed Tube Wave

FIGS. 1 and 2 show a first preferred embodiment of an instrumented transport pipe and an instrumented oil well production pipe, respectively. Both of these embodiments include pipe-mounted receivers ("permanent sensors") positioned to detect perturbed tube waves. The corresponding method for these two embodiments is as described above for the first preferred embodiment.

FIG. 2 illustrates an oil production system having a second preferred embodiment of a flow assurance measurement system for detecting and characterizing a solids deposit in an oil well production pipe. This embodiment includes a second instrumented pipe 50. Second instrumented pipe 50 includes production pipe 51, pipe-mounted transmitter 52, and pipe-mounted receivers 53–56, receivers 53–56 typically representing a much greater number of receivers. In this second preferred embodiment, tube waves propagating in both directions from transmitter 52 are utilized. (In FIG. 2, only one direction of utilization is shown). Transmitter 52 transmits a first acoustic tube wave pulse 57 that propagates in the fluid in the pipe, along the axis of the pipe. When first acoustic wave pulse 57 encounters solids deposit 59, it produces perturbed wave 58. Receivers 53–56 each receive perturbed wave 58 and produce an acoustic signal.

2) Instrumented Pipelines, Reflected Tube Wave

Figure 3:
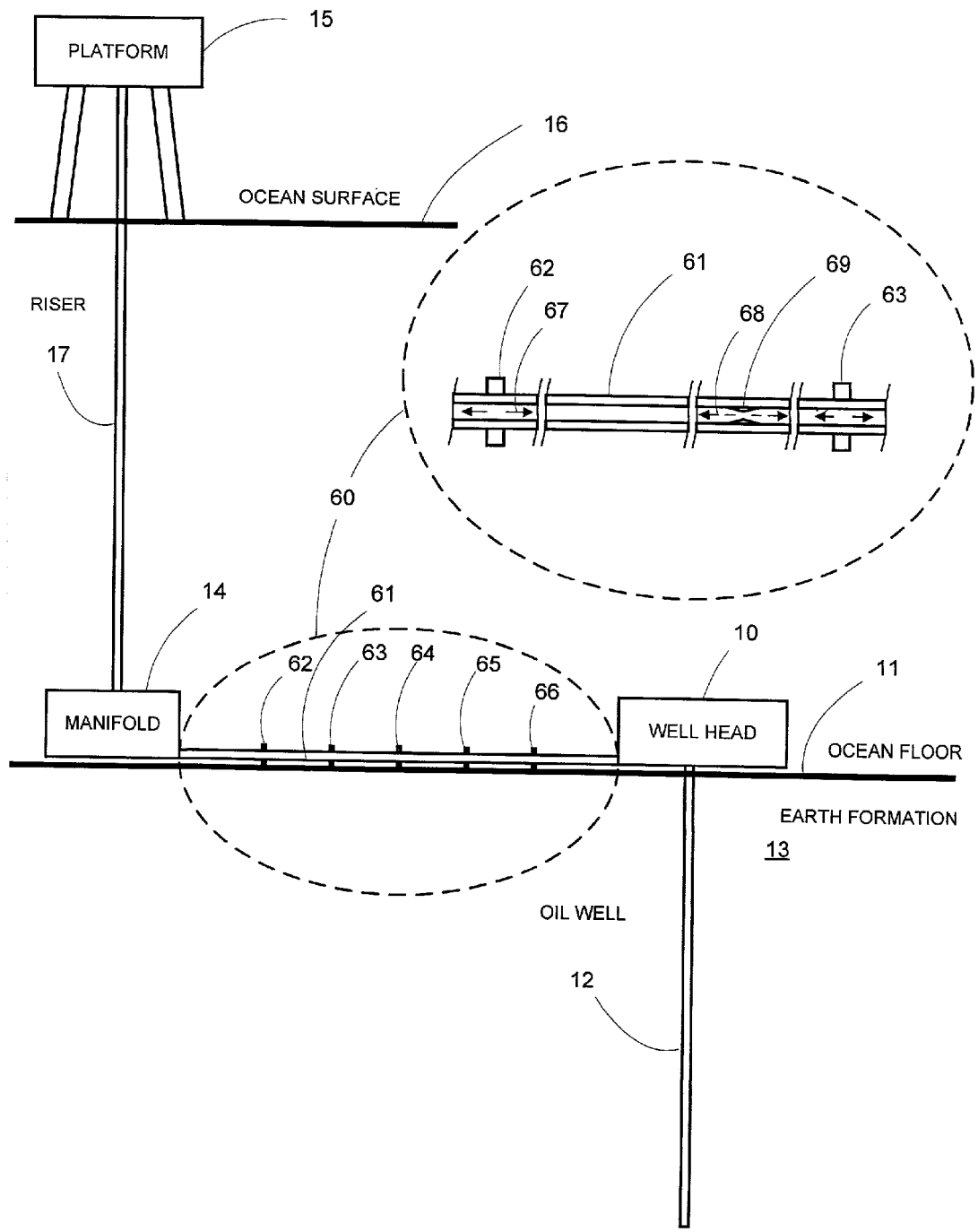
FIG. 3 illustrates a third embodiment of an instrumented transport pipe having a pipe-mounted transmitter/receiver positioned to transmit tube waves along the pipe and to detect reflected tube waves.
Figure 4:
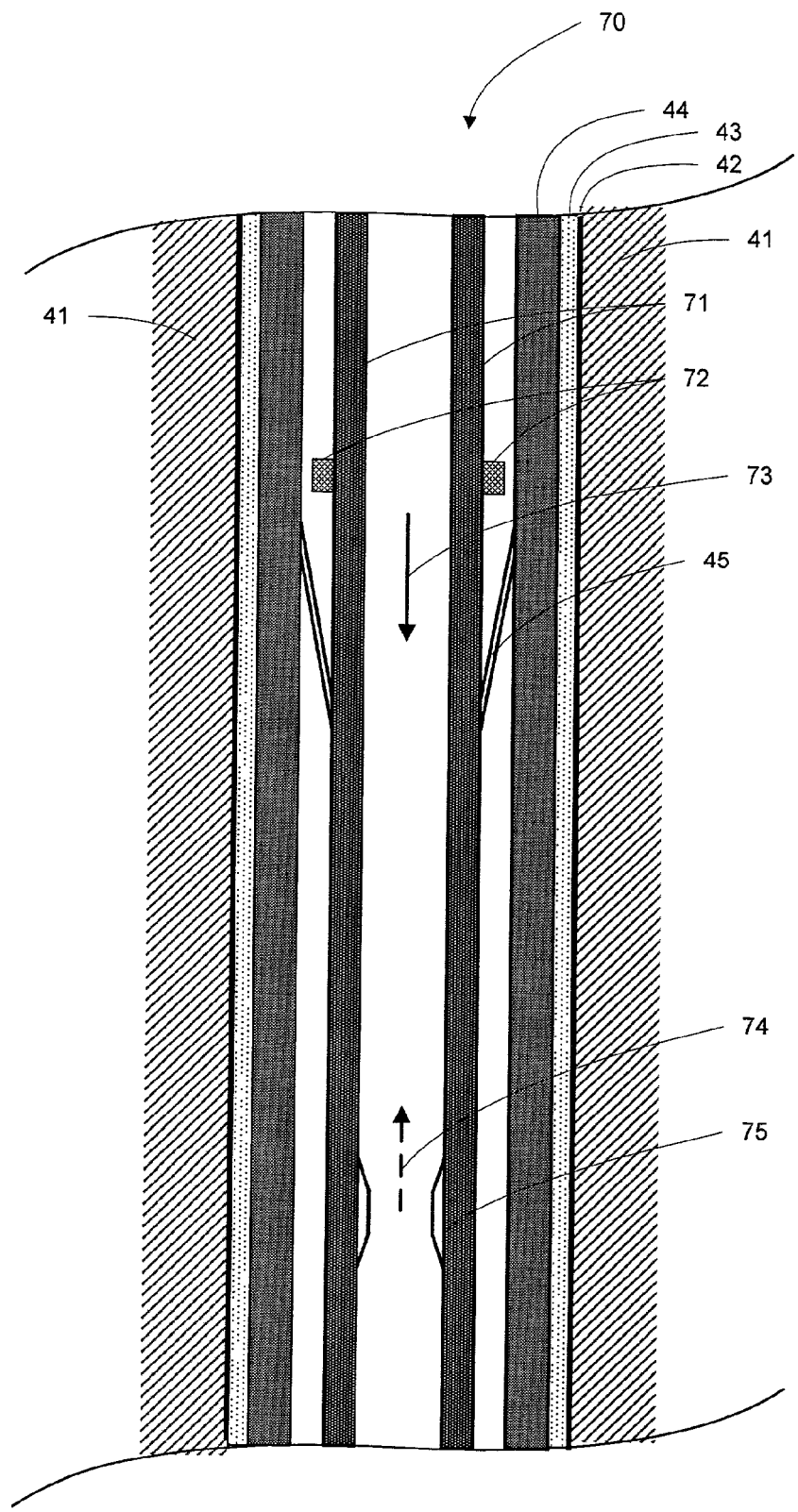
FIG. 4 illustrates a fourth embodiment of an instrumented oil well production pipe having a pipe-mounted transmitter/receiver positioned to transmit tube waves along the pipe and to detect reflected tube waves.

FIGS. 3 and 4 show an instrumented transport pipe and an instrumented oil well production pipe, respectively. Both of these embodiments include an array of pipe-mounted transmitter/receivers ("permanent transmitter/sensors"). Each transmitter/receiver includes (functionally) a transmitter and a receiver. Each transmitter is adapted to transmit a first acoustic tube wave pulse to produce a reflected wave when the first acoustic wave encounters a solids deposit in the fluid-filled pipe. Each receiver is adapted to receive a reflected acoustic tube wave produced by the first acoustic wave of its associated transmitter and to produce from the received wave an acoustic signal. Thus, a single transmitter/receiver device can be used for both transmission and reception, as is common practice in pulse-echo, sonar, and radar systems.

FIG. 3 illustrates a sub-sea oil production system having a third embodiment of a flow assurance measurement system for detecting and characterizing a solids deposit in a sub-sea transport pipe. This embodiment includes a third instrumented pipe, instrumented transport pipe 60, having pipe-mounted transmitter/receivers 62–66 positioned to transmit first acoustic wave 67 along the pipe and to detect reflected wave 68, reflected from solids deposit 69.

As described above for the first embodiment, the sub-sea oil production system includes well head 10 located at ocean floor 11, and oil well 12 extending downward into earth formation 13. In production, oil from the well is pumped through transport pipe 61 to manifold 14. Typically, multiple transport pipes are connected in like manner to manifold 14. Oil from the several transport pipes is pumped to platform 15 at ocean surface 16 via riser 17.

Instrumented pipe 60 includes a transport pipe 61 and transmitter/receivers 62–66. In a typical installation, transport pipe 61 would include a plurality of pipe joints connected in series. In an installation having a short length transport pipe, instrumented pipe 60 would preferably include only a single pair of transmitter/receivers. In an installation having a medium or long transport pipe 61, instrumented pipe 60 would preferably include multiple transmitter/receivers. Because a reflected tube wave is typically much less powerful that its originating tube wave, transmitter/receivers are spaced apart at distances much less than the spacing of receivers of the first embodiment.

In the embodiment of FIG. 3, instrumented pipe 60 preferably includes at least two transmitter/receivers. The inset in FIG. 3 shows transport pipe 61, and transmitter/receivers 62 and 63. Transmitter/receiver 62 transmits first acoustic wave pulse 67 and receives reflected wave 68, reflected from solids deposit 69.

Figure 14:
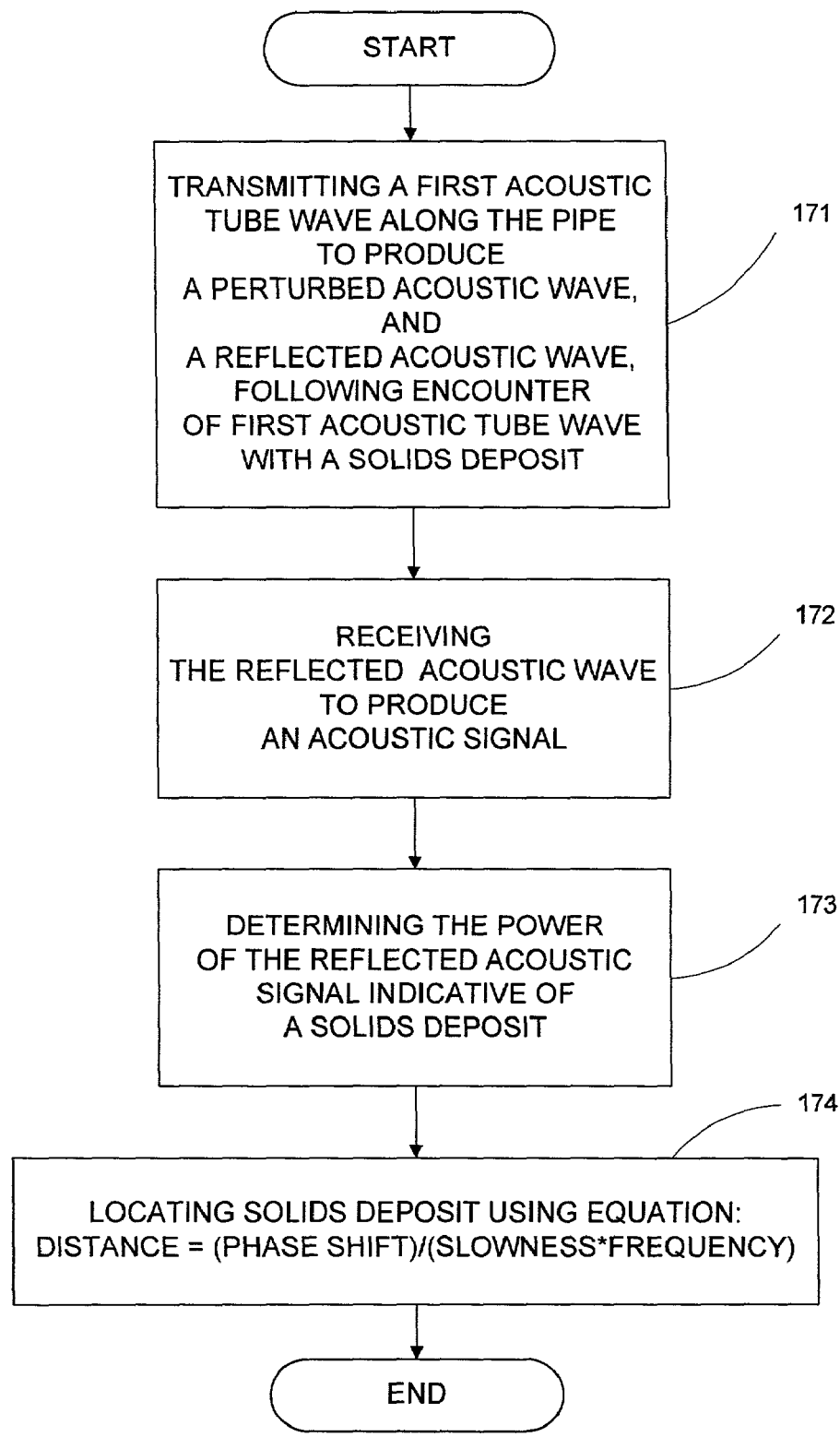
FIG. 14 illustrates the general principle of an alternative method for assessing a solids deposit by receiving a reflected tube wave and determining attenuation as indicative of a solids deposit inside a pipe.

The preferred method of assessing a solids deposit by receiving a reflected tube wave and determining power as indicative of a solids deposit inside a pipe is illustrated in FIG. 14.

FIG. 4 illustrates an oil production well system having a fourth embodiment of a flow assurance measurement system for detecting and characterizing a solids deposit in an oil well production pipe. This embodiment includes a fourth instrumented pipe, instrumented oil well production pipe 70, having a pipe-mounted transmitter/receiver 72. Transmitter/receiver 72 transmits first acoustic tube wave pulse 73 along production pipe 71 and receives reflected wave 74, reflected from solids deposit 75. FIG. 4 also shows earth formation 41 defining borehole edge 42 and cement 43 between the borehole edge and casing 44. Production tube 71 is supported by hangers 45 attached to casing 44.

3) Logging Tool, Perturbed Tube Wave

Figure 5:
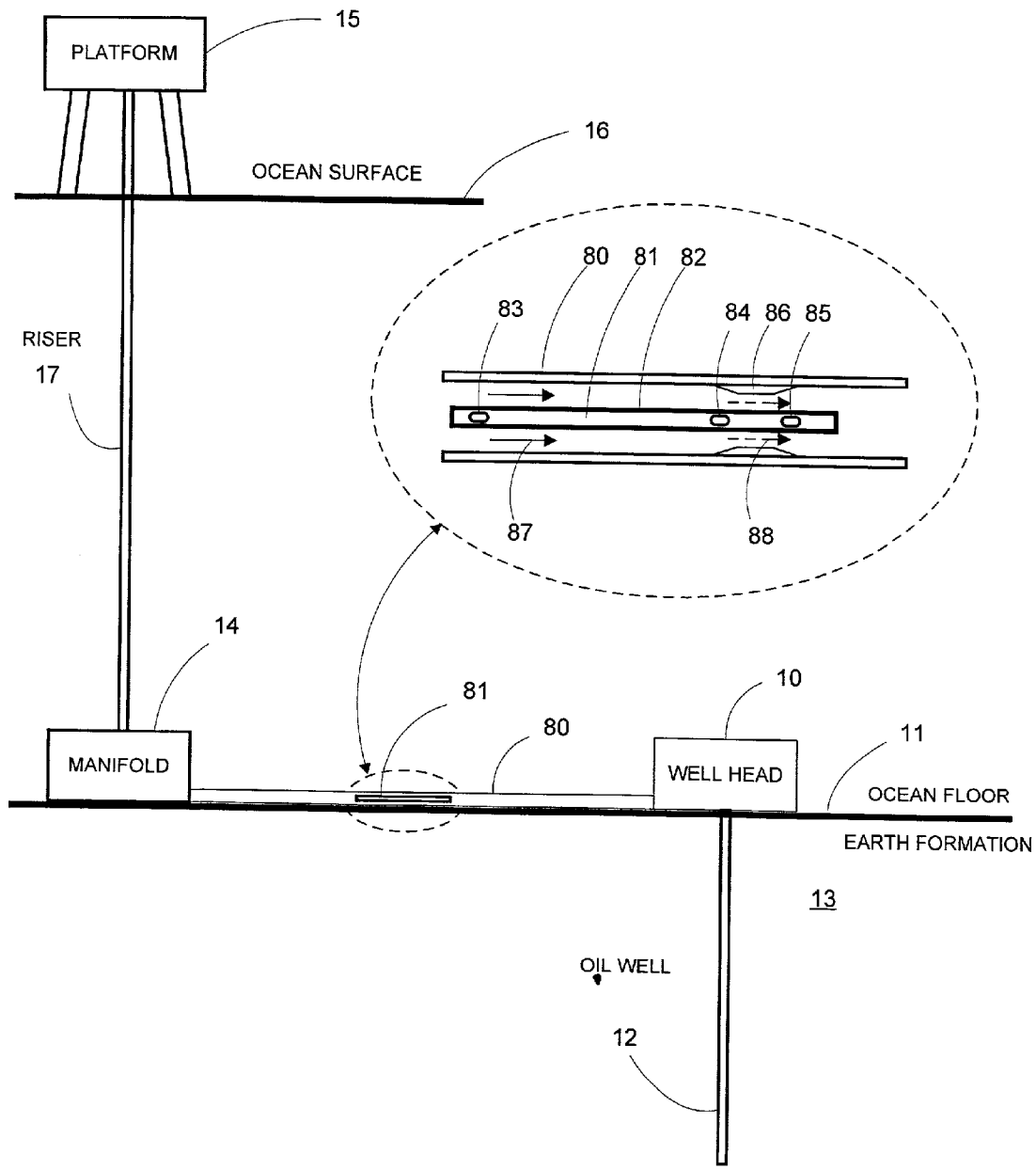
FIG. 5 illustrates a first preferred embodiment of logging tool for use in a transport pipe, the tool having receivers positioned to detect perturbed tube waves for detecting and characterizing a solids deposit in a transport pipe.
Figure 6:
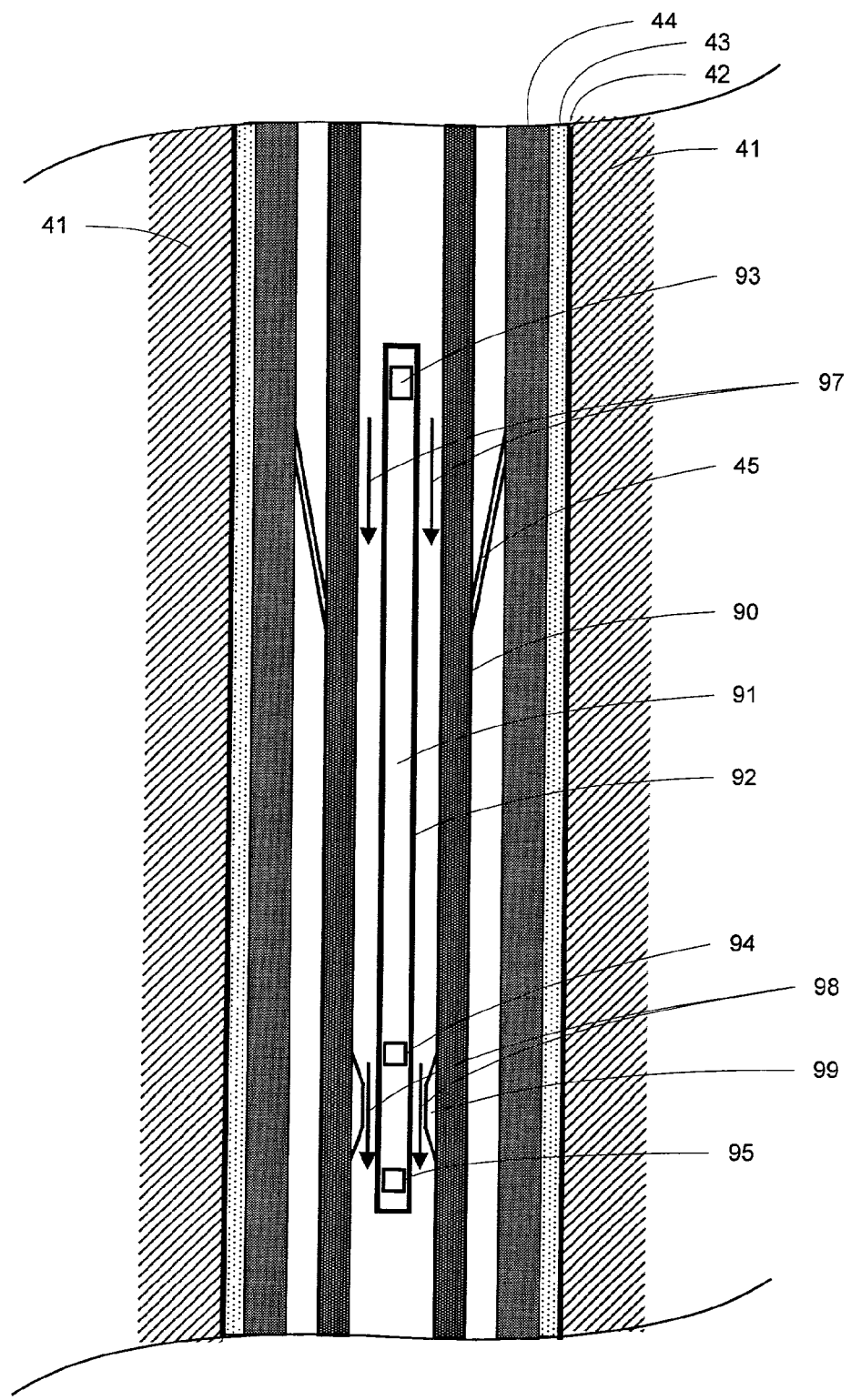
FIG. 6 illustrates a second embodiment of a logging tool for use in an oil well production pipe, the tool having receivers positioned to detect perturbed tube waves.

FIGS. 5 and 6 show an elongated logging tool, more specifically a pigging tool and a wireline tool, respectively. Both tools include receivers positioned to detect perturbed tube waves. The logging tools of FIGS. 5 and 6 are configured for pigging in a transport pipe and for wireline logging in an oil well production pipe, respectively.

Both logging tools includes an elongated housing adapted for travel within a pipe, and a transmitter attached to the elongated housing. The transmitter is adapted to transmit a first acoustic tube wave pulse. The logging tool also includes an array of receivers mounted in the elongated housing and spaced apart from the transmitter. Each receiver is adapted to receive a perturbed acoustic wave and to produce an acoustic signal. The wireline tool is conveyed by a wireline. The pigging tool is conveyed by fluid flow energy within the pipe, as is common in pigging operations.

FIG. 5 illustrates a first preferred embodiment of a logging tool 81 for detecting and characterizing a solids deposit 86 in a sub-sea transport pipe 80. Logging tool 81 has a housing 82, a tool-mounted transmitter 83 for transmitting a first acoustic tube wave pulse 87 along the transport pipe, and tool-mounted acoustic receivers 84 and 85 positioned to receive perturbed wave 88, perturbed by solids deposit 86. The preferred method of assessing a solids deposit by receiving a perturbed tube wave and determining slowness as indicative of a solids deposit inside a pipe is illustrated in FIGS. 9–11, and is discussed above in regard to the first preferred embodiment.

FIG. 6 illustrates a second embodiment of a wireline tool for detecting and characterizing a solids deposit in an oil well production pipe. Wireline tool 91 includes housing 92, a tool-mounted transmitter 93, mounted to housing 92, for transmitting acoustic tube wave pulses 97 along production pipe 90. It also includes tool-mounted acoustic receivers 94 and 95, each spaced apart from the transmitter and mounted to housing 92, positioned to receive perturbed wave 98, perturbed by solids deposit 99.

4) Logging Tool, Reflected Tube Wave

Figure 7:
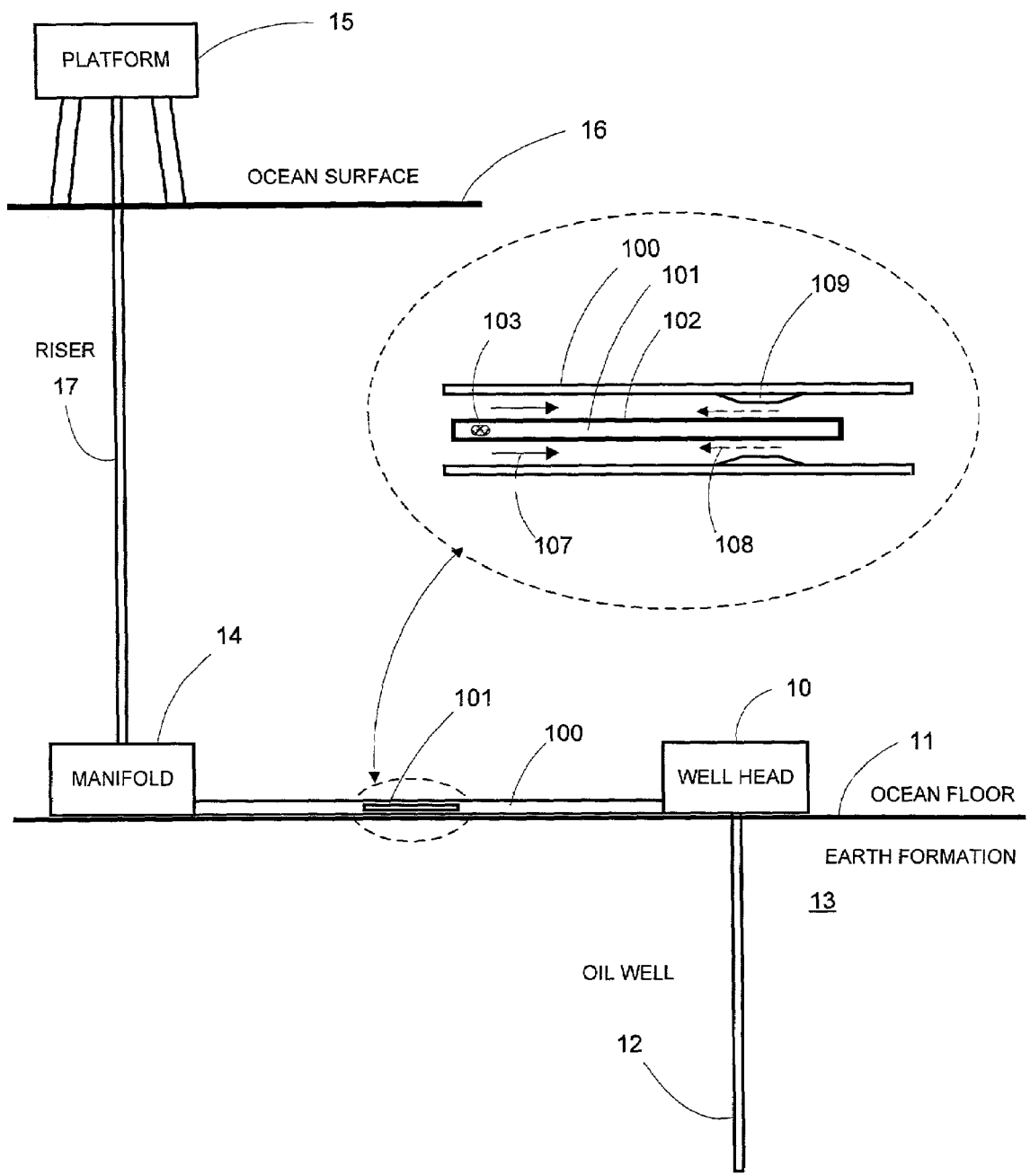
FIG. 7 illustrates a third embodiment of a logging tool for use in a transport pipe, the tool having a transmitter/receiver positioned to transmit tube waves along the pipe and to detect reflected tube waves.

FIGS. 7 and 8 show an elongated logging tool, more specifically a pigging tool and a wireline tool, respectively. Both tools include a receiver positioned to detect reflected tube waves. The logging tools of FIGS. 7 and 8 are configured for pigging in a transport pipe and for wireline logging in an oil well production pipe, respectively.

Both logging tools includes an elongated housing adapted for travel within a pipe, and a transmitter/receiver within the elongated housing. The transmitter/receiver is adapted to transmit a first acoustic tube wave pulse, to receive a reflected acoustic tube wave, and to produce an acoustic signal.

FIG. 7 illustrates a third embodiment of a logging tool for detecting and characterizing a solids deposit in a sub-sea transport pipe. FIG. 7 illustrates a sub-sea oil production system having a third embodiment of a logging tool for detecting and characterizing a solids deposit in a sub-sea transport pipe 100. Third logging tool 101 includes housing 102, a tool-mounted transmitter/receiver 103, mounted to housing 102, for transmitting first acoustic waves 107 along production pipe 100. The receivers of transmitter/receiver 103 receive reflected wave 108, reflected by solids deposit 109. The preferred method of assessing a solids deposit by receiving a reflected tube wave and determining power as indicative of a solids deposit inside a pipe is illustrated in FIG. 14, and is discussed above as used in the embodiment of FIG. 3.

FIG. 8 illustrates a fourth embodiment of a wireline tool for detecting and characterizing a solids deposit in production pipe 110 of a production oil well. Fourth wireline tool 111 includes a housing 112, and tool-mounted transmitter/receiver 113 for transmitting a first acoustic tube wave pulse 117 along production pipe 110. Transmitter/receiver 113 receives reflected wave 118, produced when first acoustic wave 117 encounters solids deposit 119. The method of the fourth logging tool embodiment is substantially the same as the method of the third logging tool embodiment.

A hybrid embodiment (not illustrated) includes an instrumented pipe having one or more transmitters and a logging tool having an array of receivers.

Theory of Tube Waves and Reflected Tube Waves

Imagine a sound pulse is generated in the fluid in a pipe. The energy of this pulse, which is confined essentially within the fluid, propagates at a calculable speed, nearly equal to the speed of sound in the fluid. The wave in this fluid-trapped mode is generally known as the tube wave. We imagine that there is a relatively well-defined pulse in the time domain, which may or may not be narrow-band in the frequency domain. It propagates with very little distortion, and very little loss, under the uniform conditions of a stiff, clean pipe containing a single, clean liquid. According to well-understood acoustic principles, upon hitting changes in these conditions, such as the waxes, asphaltenes, scale, or hydrate deposits, the tube wave will both be reflected and perturbed. That is, some energy will be reflected from this change in wall conditions, back toward the source. Upon hitting these deposits, the propagating wave will continue on, having been perturbed in frequency and time by the constriction. Thus, one can use the reflected energy, or the propagating pulse, or both, to characterize the deposition.

In theory and in practice, the tube wave is a very energetic, robust signal that can propagate long distances. The tube wave is used in sonic logging to measure permeability. It is also used for telemetry in LWD (logging while drilling) tools. The tube wave is an excellent candidate for interrogating miles of pipe in an efficient manner.

According to well-understood acoustic principles, when a tube wave propagating away from its source comes upon changes in the pipe conditions, such as depositional constriction of the inner diameter, there will be a reflected tube wave which will propagate back towards the source. This reflected pulse can then be detected and digitized near or at the source. An analysis of the time sequence of the reflected pulse, as compared against the originally transmitted pulse, serves to give information about the location and shape of the constriction.

Two simple extremes serve to illustrate the point, although the assumptions entering into these examples need not be satisfied in order for the measurement to be a useful indicator of constrictions. The distinction is whether the constriction occurs abruptly, i.e., over a length that is shorter than the tube wave's dominant wavelength, or whether it occurs gradually over many wavelengths. It will be further assumed that the constriction is made of an acoustically "stiff" material, relative to the fluid in the pipe. Let us suppose that the cross-sectional area of the pipe varies with axial position as $A_{(z)}$, with the convention that the unconstricted area of the pipe is $A_0$.

1) Suppose the cross-sectional area changes abruptly from $A_0$ to $A_1$ at some location. The reflected pulse has essentially the same shape as the incident pulse, but having an amplitude given by:

$$R = \frac{A_0 - A_1}{A_0 + A_1}$$

The time at which the pulse arrives is T=2d/c after the initial pulse, where d is the distance to the constriction and c is the speed of the tube wave.

2) Suppose the cross-sectional area, $A_{(z)}$, changes in a continual fashion, over a distance which is large compared against the wavelength. The amplitude of the reflected wave is now frequency dependent and is now given approximately as:

$$R(\omega) = -\frac{1}{2}\int_{-\infty}^{\infty} \frac{d}{dz}[\ln(A(z)/A_0)]\exp(2i\omega z/c)dz$$

In cases in which neither approximately 1) or 2) holds true, especially taking into account the compressibility of the deposited material, a more complicate d numerical analysis must be employed. The point is that the reflected pulse can be analyzed with standard techniques to determine the location and shape of the constriction. The delay time gives the location and the spectral content gives the shape.

Test Results Using Perturbed Tube Waves

The inventors conducted experiments to show that propagating tube waves can be used to detect and quantify changes at the pipe walls due to material depositions.

An experiment simulating a transport-pipe with an evolving wax blockage, was performed using a 5 ft. long, 0.750" ID/1.00" OD, stainless steel pipe. Wax was chosen as the blockage material based mainly on its ease of fabrication, as a series of simulated deposits, each one having a specific thickness of wax, were constructed by dipping the pipe into liquid wax (much like candle-making). Beeswax was chosen because its acoustic properties are similar to the precipitate waxes expected.

Figure 15:
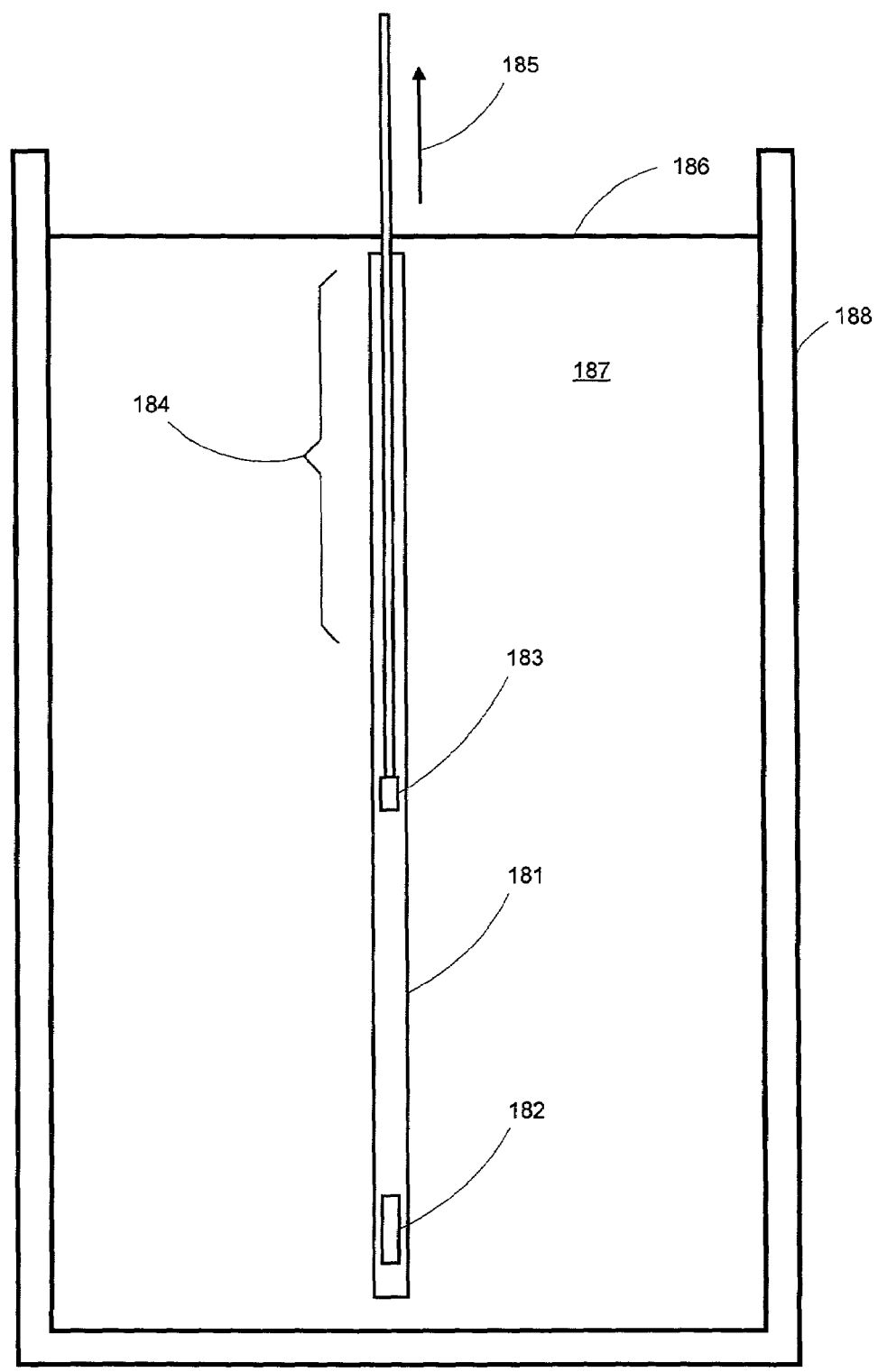
FIG. 15 shows test equipment used to test methods for detecting a solids deposit inside a pipe using perturbed tube waves.

FIG. 15 shows the test equipment used. Transmitter 182 and receiver 183, both B&K 8103 hydrophones, were located inside, and approximately centered in, pipe 181. Pipe 181 was submerged in water 187 contained by water tank 188 to water level 186 to ensure a liquid-fill. Transmitter 182 was fixed at the bottom of pipe 181. Receiver 183 was translatable along the pipe length, and was scanned, by moving receiver 183 up as indicated by arrow 185, from a position 30 inch (approximately 76 cm) below the top of the pipe, up to the top of the pipe. The first scan was performed on a clean free-pipe, representing no blockage problem. Then, layers of wax were added to region 184 of the inner walls of the pipe, starting from 20 inch (approximately 51 cm) below the top of the pipe, to the top of the pipe. Pipe 181 was re-scanned with each additional wax layer added and the data was processed and compared to the clean-pipe results.

Figure 16:
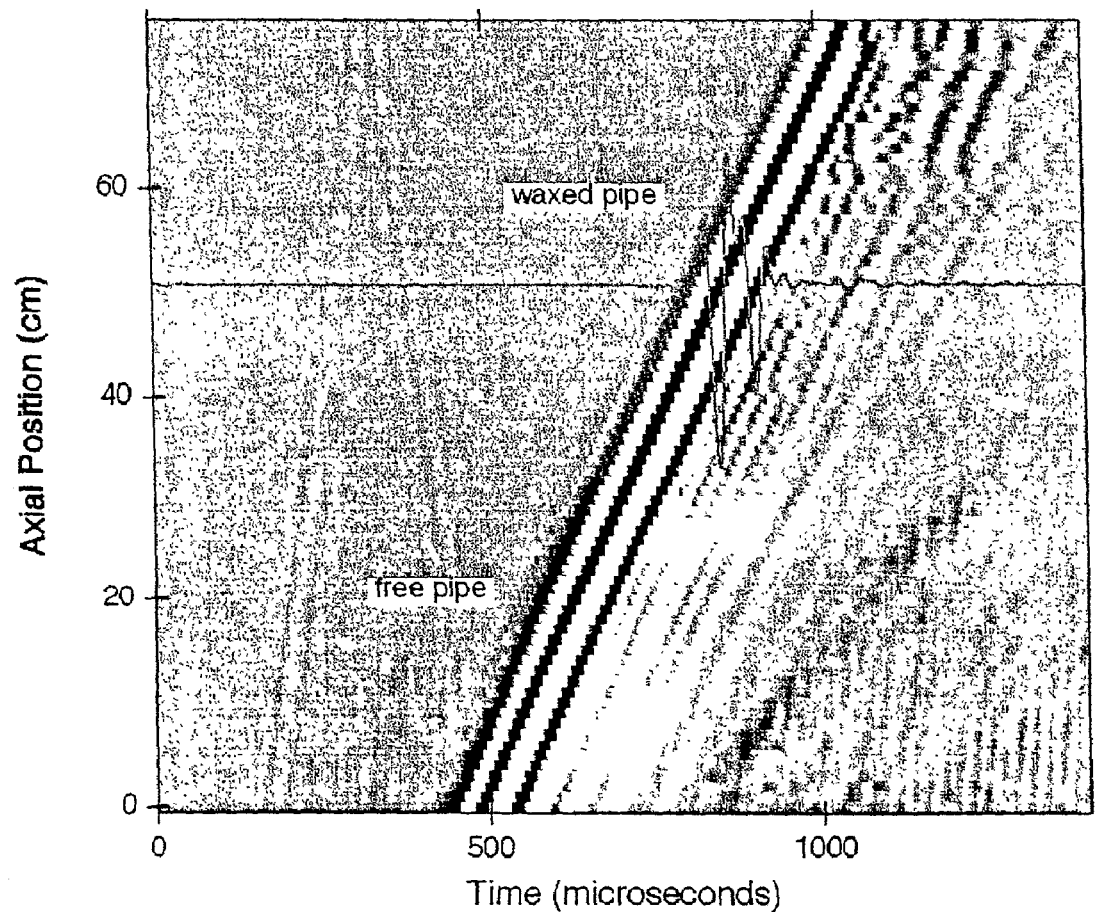
FIG. 16 is a variable-density plot of a waveform scan in a pipe that has an internal wax layer over half the length of the pipe, obtained using the apparatus of FIG. 15.

FIG. 16 shows waveforms obtained over the 30 inch (approximately 76 cm) receiver scan, presented as a variable-density log (VDL), for the case of the pipe having a 0.025 inch (approximately 0.06 cm) layer of wax build-up on the inner walls. This layer thickness represents a 6.7% reduction in diameter of open pipe, simulating an early stage of solids deposition. The tube wave is the dominant arrival in the plot. A representative waveform from the scan is overlaid on the VDL image. Faint, early arrivals seen before the tube wave are the steel modes, such as the extensional wave in the pipe (and its reflection wave). In the early section of the scan (0 to 30 cm), the receiver is entirely in the region of clean-pipe. In the clean-pipe, the tube wave propagates at a constant speed and attenuation is virtually zero, as indicated by the constant weight of the black and white lines. This is as expected.

As the receiver scanned up the pipe, it passed from the clean-pipe section, into the wax-layered section, at about 32 cm. Upon reaching the wax, the tube wave was propagating at a slower speed (evidenced by the new slope) and with greater attenuation. Note that the amplitude decreases as the scan progresses further into the wax. This thin wax layer is seen to be affecting both the amplitude and velocity of the tube wave in the pipe. As expected, attenuation is seen to increase and the velocity is seen to decrease.

Figure 17:
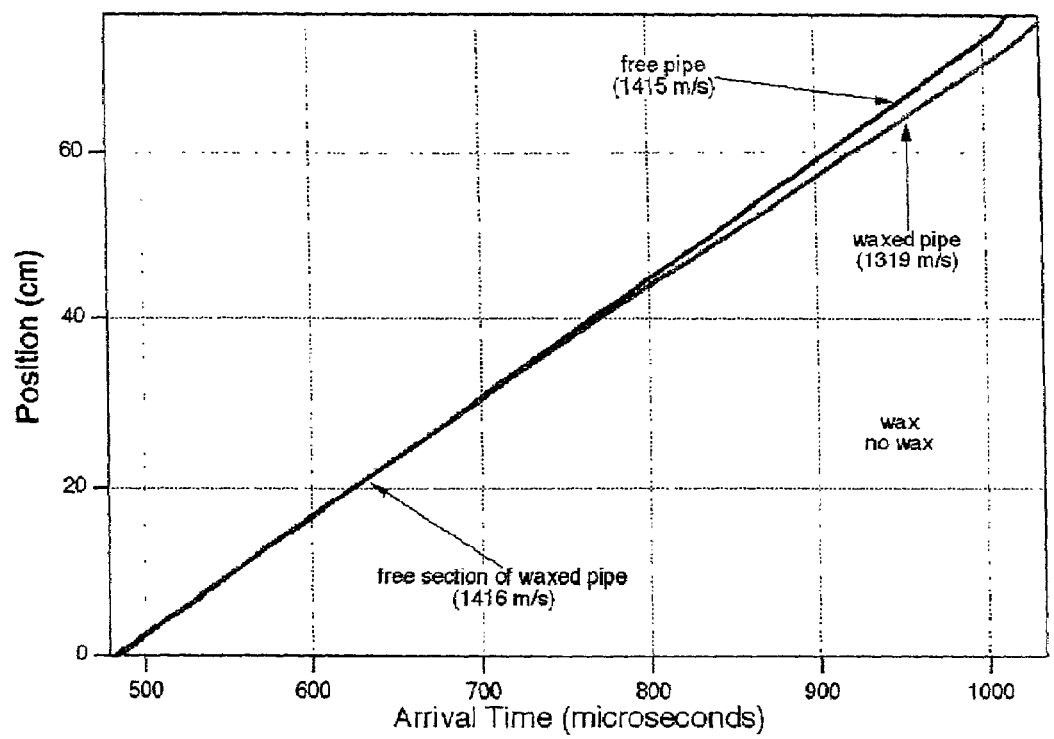
FIG. 17 shows tube-wave arrival times in free pipe and waxed pipe.

FIG. 17 shows tube-wave arrival times in free pipe and waxed pipe based on a simple "first-zero-crossing" processing technique on these waveforms. The slopes of the lines indicate velocity. FIG. 17 clearly shows a wax layer increases the arrival times of a tube wave, i.e., increases slowness. This technique is not robust, and it does not provide dispersions, but it is easy to understand and it provides some validation for the TKO techniques used to obtain the plots of FIGS. 18A and 18B below. As noted above, TKO is a frequency-based technique for sonic waveform processing that provides slowness and attenuation data as a function of frequency.

Figure 18A:
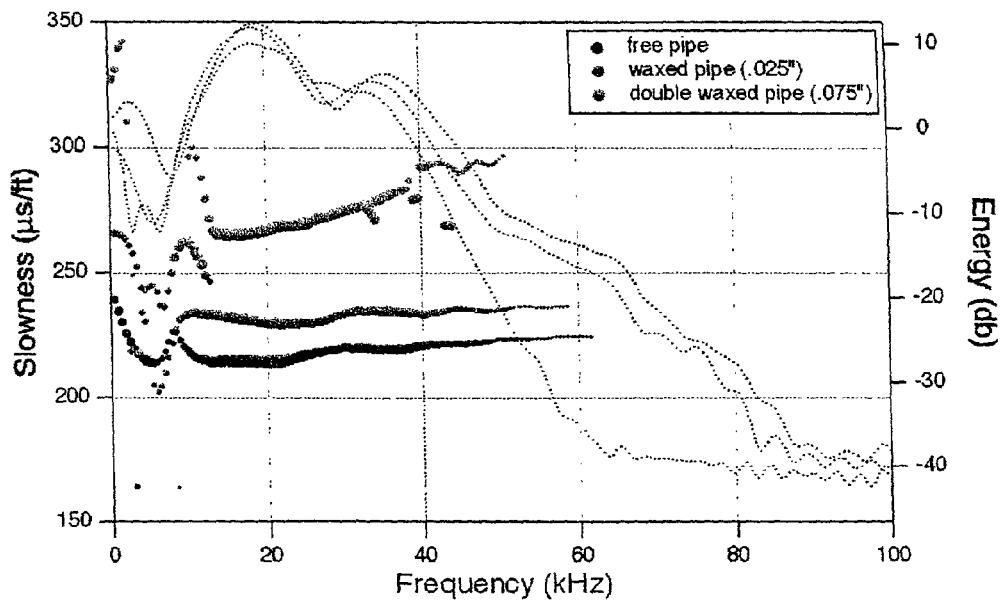
FIG. 18A is a graph showing tube-wave dispersal curves for free and waxed pipes showing slowness as a function of frequency.
Figure 18B:
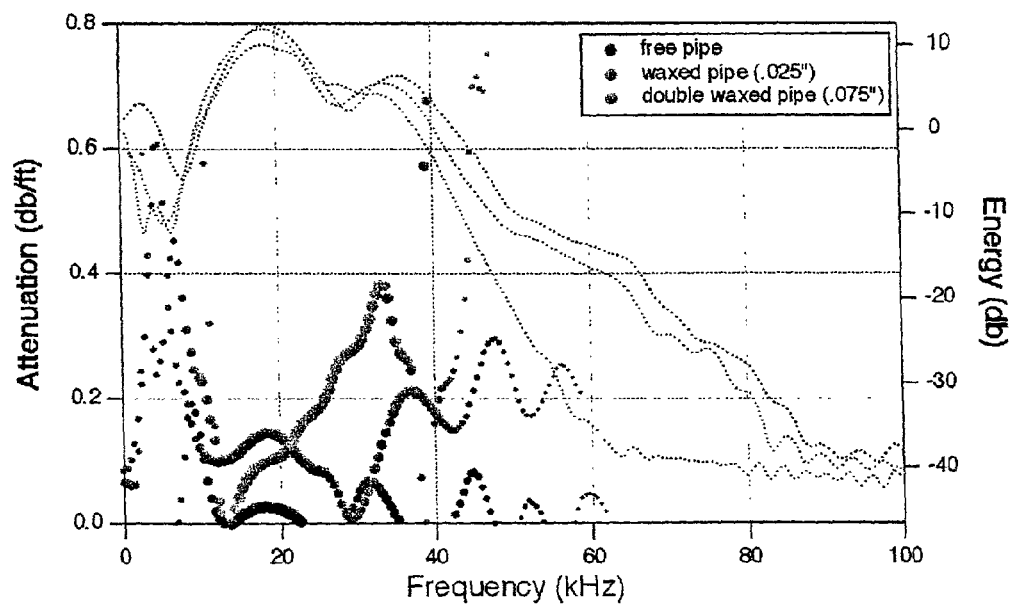
FIG. 18B is a graph showing tube-wave dispersal curves for free and waxed pipes showing attenuation as a function of frequency.

FIGS. 18A and 18B are TKO-derived dispersion curves for the experiment described above, plus another experiment with a thicker wax layer. This second layer reached 0.075", representing a 20 percent decrease in pipe diameter. We view this degree of blockage as being within the realm of serious.

FIG. 18A shows slowness (1/velocity) as a function of frequency for all three conditions. It is seen from this plot that slowness increases as the wax layer increases. Also, the thicker layer of wax exhibits considerably more dispersion, indicating a significantly higher attenuation of the wave. On the same plot, the frequency spectrum of a waveform is shown for each wax condition. The loss of high frequencies as wax builds up is caused by attenuation.

FIG. 18B shows attenuation as a function of frequency. FIG. 18B shows a strong contrast between the zero-attenuation (centered on zero) of the clean-pipe and the increasing attenuation for thicker wax layers. The waviness of the attenuation curves is caused by interference with other modes. Slowness is less sensitive to this interference.

Figure 19:
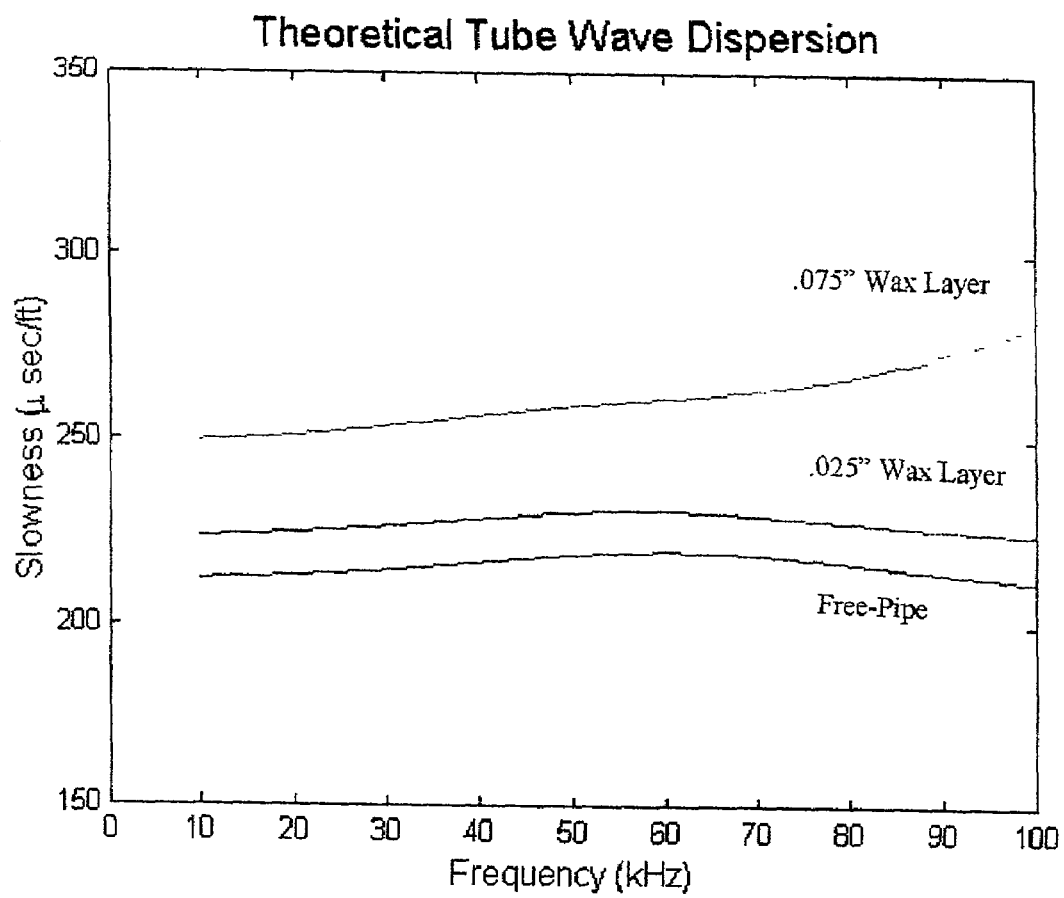
FIG. 19 is a graph showing theoretical predictions of tube-wave dispersal curves for free and waxed pipes, indicating that predictions match experimental results.

FIG. 19 shows the theoretical results obtained using a mathematical model. For each of the three thickness wax layers, there is good agreement with the experiment for both the absolute values of slowness as well as the general trends. The model seems to match the free-pipe and 0.025" layer somewhat better than it matches the thicker, 0.075" layer. This may be due to small inaccuracies in the acoustic parameters (measured values) of our beeswax, or in the measured values of the layer thickness in the experiment.

What is claimed is:

1. A method for detecting a solids deposit inside a long fluid-filled pipe, comprising:
   transmitting a first acoustic tube wave along said pipe to produce two deposit-modified acoustic tube waves, including a perturbed acoustic tube wave and a reflected acoustic tube wave, following encounter of said first acoustic tube wave with a solids deposit;
   receiving a deposit-modified acoustic tube wave to produce at least one acoustic signal; and
   determining the value of a selected characteristic of said at least one acoustic signal indicative of a solids deposit in said pipe.

2. A method according to claim 1, wherein receiving a deposit-modified acoustic tube wave includes receiving a perturbed acoustic tube wave at the at least one pair of spaced-apart first and second receivers to produce first and second acoustic signals; and wherein determining the value of a selected characteristic includes using TKO processing to produce slowness spectrum data and attenuation spectrum data.

3. A method according to claim 1, further including moving a pair of receivers within the interior of said pipe to a succession of positions along said pipe.

4. A method according to claim 1, further including moving a logging tool, including one transmitter and a distant pair of spaced-apart receivers, within the interior of said pipe to a succession of positions along said pipe.

5. A method according to claim 1, wherein said deposit-modified acoustic tube wave is a perturbed acoustic tube wave, and wherein said selected characteristic is attenuation.

6. A method according to claim 1, further including moving one transmitter/receiver within the interior of the pipe to a succession of positions along said pipe.

7. A method according to claim 1, wherein said selected characteristic is slowness, the method further comprising:
   determining an initial value of said selected characteristic during initial production;
   determining a later value of said selected characteristic during production; and subtracting said initial value from said later value to produce a difference value indicative of an increase in thickness of a solids deposit.

8. A method according to claim 7, further comprising:
   using said difference value together with material parameter data of a selected deposited material to produce an estimate of thickness of said solids deposit;
   wherein said selected deposited material is selected based on an engineering determination of most likely deposited material.

9. A method according to claim 1, wherein said deposit-modified acoustic tube wave is a reflected acoustic tube wave, and wherein said selected characteristic is power.

10. A method according to claim 9, further determining an average value of slowness over a length of pipe adjacent to a transmitter, and locating the solids deposit using the equation: distance=(transit time)/(2*average slowness).

11. A method for locating a solids deposit inside a long fluid-filled pipe, comprising:
   transmitting a first acoustic tube wave along said pipe to produce two deposit-modified acoustic tube waves, including a perturbed acoustic tube wave and a reflected acoustic tube wave, following encounter of said first acoustic tube wave with a solids deposit; and
   receiving the perturbed acoustic tube wave at a pair of spaced-apart first and second receivers to produce first and second acoustic signals whose times of arrival at said first and second receivers are indicative of direction and distance of a solids deposit.

12. A method for determining type of a solids deposit inside a long fluid-filled pipe, comprising:
   transmitting a first acoustic tube wave along said pipe to produce two deposit-modified acoustic tube waves, including a perturbed acoustic tube wave and a reflected acoustic tube wave, following encounter of said first acoustic tube wave with a solids deposit;
   receiving the perturbed acoustic tube wave at a pair of spaced-apart first and second receivers to produce first and second acoustic signals;

digitizing said first and second acoustic signals to produce time-based digital data;

performing FFT on said time-based digital data to produce frequency-based digital data;

subtracting phase associated with said second acoustic signal from phase associated with said first acoustic signal to produce a phase difference for each of a plurality of frequencies;

multiplying each phase difference by its associated frequency; and dividing the result by the distance between said first and second receivers to produce slowness spectrum data, indicative of type of a solids deposit.

13. A method according to claim 12, further comprising:
subtracting power associated with said second acoustic signal from power associated with said first acoustic signal to produce a power difference for each of a plurality of frequencies; and dividing power difference by the distance between said first and second receivers to produce attenuation spectrum data.

14. A method according to claim 13, further comprising:
determining the thickness of said solids deposit using inversion model to process said slowness spectrum data, said power spectrum data, and material parameter data.

15. A method according to claim 14, wherein said material parameter data is derived from an engineering judgment determination of the most likely deposited material.

16. A method according to claim 14, further identifying the location of said solids deposit as being between said first and second receivers.

17. A method for determining slowness of a solids deposit inside a long fluid-filled pipe, comprising:
transmitting a first acoustic tube wave along said pipe to produce two deposit-modified acoustic tube waves, including a perturbed acoustic tube wave and a reflected acoustic tube wave, following encounter of said first acoustic tube wave with a solids deposit;
receiving a perturbed acoustic tube wave at spaced-apart first and second receivers to produce first and second acoustic signals; and
determining the value of a selected characteristic of said at least one acoustic signal indicative of a solids deposit in said pipe;
wherein determining the value of a selected characteristic includes subtracting time of arrival of said first acoustic signal from time of arrival of said second acoustic signal to determine slowness.

18. A permanent-sensor flow assurance measurement system for detecting a solids deposit inside a long fluid-filled pipe, said system comprising:
a long instrumented pipe including:
a long pipe;
an acoustic tube wave transmitter attached to said pipe positioned to transmit a first acoustic tube wave along said pipe; and
an array of acoustic tube wave receivers, said array aligned with said pipe, said receivers attached to said pipe, said array spaced apart from said transmitter, each of said receivers adapted to receive a perturbed acoustic tube wave propagating along said pipe and to produce from the perturbed acoustic tube wave an acoustic signal; and
means for processing acoustic signals to determine the value of a selected characteristic of an acoustic tube wave indicative of a solids deposit in a the long fluid-filled pipe.

19. A long instrumented pipe for use in a permanent-sensor flow assurance measurement system for detecting a solids deposit inside a long fluid-filled pipe, said instrumented pipe comprising:
a long pipe;
an acoustic tube wave transmitter attached to said pipe positioned to transmit a first acoustic tube wave along said pipe; and
an array of acoustic tube wave receivers, said array aligned with said pipe, said receivers attached to said pipe, said array spaced apart from said transmitter, each of said receivers positioned to receive a perturbed acoustic tube wave propagating along said pipes and to produce from the perturbed acoustic tube wave an acoustic signal indicative of a solids deposit in the long fluid-filled pipe.

20. A permanent-sensor flow assurance measurement system for detecting a solids deposit inside a long fluid-filled pipe, said system comprising:
a long instrumented pipe including:
a long pipe and an array of acoustic tube wave transmitter/receivers, said array aligned with said pipe, each transmitter/receiver attached to said pipe, each transmitter/receiver having a transmitter function and a receiver function, each transmitter/receiver positioned to transmit a first acoustic tube wave along said pipe to produce a reflected acoustic tube wave when said first acoustic tube wave encounters a solids deposit in said fluid-filled pipe, each transmitter/receiver positioned to receive a reflected acoustic tube wave produced from its first acoustic tube wave, and adapted to produce therefrom an acoustic signal; and
means for processing acoustic signals to determine the value of a selected characteristic of an acoustic tube wave indicative of a solids deposit in a the long fluid-filled pipe.

21. A long instrumented pipe for use in a permanent-sensor flow assurance measurement system for detecting a solids deposit inside a long fluid-filled pipe, said instrumented pipe comprising:
a long pipe; and
an array of acoustic tube wave transmitter/receivers, said array aligned with said pipe, each transmitter/receiver attached to said pipe, each transmitter/receiver having a transmitter function and a receiver function, each transmitter/receiver positioned to transmit a first acoustic tube wave along said pipe to produce a reflected acoustic tube wave when said first acoustic tube wave encounters a solids deposit in said fluid-filled pipe, each transmitter/receiver positioned to receive a reflected acoustic tube wave produced from its first acoustic tube wave, and adapted to produce therefrom an acoustic signal indicative of a solids deposit in the lone fluid-filled pipe.

22. A method for assessing a solids deposit inside a long fluid-filled pipe, comprising:
transmitting a first acoustic tube wave along said pipe to produce two deposit-modified acoustic tube waves, including a perturbed acoustic tube wave and a reflected acoustic tube wave, following encounter of said first acoustic tube wave with a solids deposit;
receiving a deposit-modified acoustic tube wave to produce at least one acoustic signal; and
determining the value of a selected characteristic of said at least one acoustic signal indicative of a solids deposit in said pipe.

* * * * *